US010697447B2

(12) United States Patent
Wegener et al.

(10) Patent No.: US 10,697,447 B2
(45) Date of Patent: Jun. 30, 2020

(54) MAGNET-BASED SYSTEMS AND METHODS FOR TRANSFERRING FLUID

(71) Applicant: Fenwal, Inc., Lake Zurich, IL (US)

(72) Inventors: Christopher J. Wegener, Libertyville, IL (US); Mark Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 442 days.

(21) Appl. No.: 14/464,753

(22) Filed: Aug. 21, 2014

(65) Prior Publication Data
US 2016/0051740 A1 Feb. 25, 2016

(51) Int. Cl.
*F04B 43/04* (2006.01)
*A61M 1/10* (2006.01)
(Continued)

(52) U.S. Cl.
CPC ........... *F04B 43/04* (2013.01); *A61M 1/1055* (2014.02); *F04B 43/025* (2013.01); *F04B 45/04* (2013.01);
(Continued)

(58) Field of Classification Search
CPC .. A61M 1/1055; A61M 1/1006; A61M 1/367; A61M 1/302; A61M 2205/128; A61M 1/1037; A61M 1/1049; F04B 43/067; F04B 43/04; F04B 43/021; F04B 45/04; F04B 43/00; F04B 43/02; F04B 43/06; F04B 45/053; F04B 45/0533; F04B 53/14; F04B 53/147; F04B 53/16; F04B 53/22; F04B 43/0054; F04B 43/028; F04B 45/045; F04B 45/047; F04B 53/162;
(Continued)

(56) References Cited

U.S. PATENT DOCUMENTS

| 2,354,958 A | * | 8/1944 | Loweke | ..... F04B 9/06 417/559 |
| 2,407,792 A | * | 9/1946 | McMillan | ..... F04B 43/0036 137/516.15 |

(Continued)

FOREIGN PATENT DOCUMENTS

| GB | 2152151 A | * | 7/1985 | ............... F04B 9/133 |
| WO | WO 2010128914 A1 | * | 11/2010 | ........... A61M 5/1413 |

OTHER PUBLICATIONS

U.S. Appl. No. 14/464,753—How are Magnets Made.*

*Primary Examiner* — Patrick Hamo
*Assistant Examiner* — Chirag Jariwala
(74) *Attorney, Agent, or Firm* — Cook Alex Ltd.

(57) ABSTRACT

A system is provided for pumping fluid, with the system including a fluid pump and a cassette. The pump includes a motor and a piston that is movable toward and away from a flexible diaphragm of the cassette. A linkage connects the motor and the piston to move the piston toward and away from the diaphragm. At least a portion of the piston or the diaphragm is magnetized, with the other having at least a portion that is magnetized or formed of a ferromagnetic material, thereby magnetically coupling the piston and the diaphragm such that movement of the piston moves the diaphragm into and out of a cassette cavity aligned with the diaphragm and piston. Movement of the diaphragm into and out of the cavity changes the effective volume of the cavity, which has the effect of drawing fluid into or forcing fluid out of the cavity.

17 Claims, 11 Drawing Sheets

(51) Int. Cl.
*F04B 45/04* (2006.01)
*F04B 43/02* (2006.01)

(52) U.S. Cl.
CPC ......... *A61M 1/1037* (2013.01); *A61M 1/1049* (2014.02); *A61M 2205/128* (2013.01)

(58) Field of Classification Search
CPC .. F04B 43/025; F04B 43/0045; F04B 43/0018; F04B 43/0081; F04B 45/10
USPC .............................. 417/413.1, 322, 480, 497
See application file for complete search history.

(56) References Cited

U.S. PATENT DOCUMENTS

| | | | | | |
|---|---|---|---|---|---|
| 2,763,253 | A * | 9/1956 | Murrah | ...................... | F01L 1/00 123/511 |
| 3,034,450 | A * | 5/1962 | Kruckeberg | .............. | F04B 9/14 137/512.4 |
| 3,515,966 | A * | 6/1970 | Marius | ...................... | G04C 3/00 310/17 |
| 3,671,814 | A * | 6/1972 | Dick | .......................... | G05F 7/00 361/154 |
| 3,774,390 | A * | 11/1973 | Dauvergne | .............. | F01K 21/04 123/66 |
| 4,236,880 | A | 12/1980 | Archibald | | |
| 4,334,838 | A * | 6/1982 | Fessler | ................ | F04B 43/0054 417/395 |
| 4,360,324 | A * | 11/1982 | Ohara | .................. | A61M 1/106 417/388 |
| 4,657,490 | A * | 4/1987 | Abbott | .............. | A61M 5/14224 417/478 |
| 4,786,240 | A * | 11/1988 | Koroly | ................... | F04B 45/04 417/413.1 |
| 4,990,066 | A * | 2/1991 | Kern | ...................... | F04B 7/0053 417/307 |
| 5,011,380 | A * | 4/1991 | Kovacs | ................... | B29C 33/40 417/413.1 |
| 5,074,757 | A * | 12/1991 | Horn | ...................... | F04B 43/009 417/395 |
| 5,186,615 | A * | 2/1993 | Karliner | ................ | F04B 43/067 417/387 |
| 5,252,044 | A * | 10/1993 | Raines | .............. | A61M 5/14228 417/479 |
| 5,385,540 | A * | 1/1995 | Abbott | ................ | A61M 1/3664 128/DIG. 3 |
| 5,476,368 | A * | 12/1995 | Rabenau | ................ | F04B 53/101 417/395 |
| 5,554,013 | A * | 9/1996 | Owens | .............. | A61M 5/14224 417/413.1 |
| 5,599,174 | A * | 2/1997 | Cook | ...................... | F04B 43/04 310/17 |
| 5,868,696 | A | 2/1999 | Giesler et al. | | |
| 5,969,385 | A * | 10/1999 | Nathanson | ............ | H01L 27/092 257/347 |
| 5,989,423 | A | 11/1999 | Kamen et al. | | |
| 6,074,178 | A * | 6/2000 | Bishop | .................. | F04B 17/003 310/328 |
| 6,208,497 | B1 * | 3/2001 | Seale | ........................ | F01L 9/04 361/154 |
| 6,280,406 | B1 | 8/2001 | Dolecek et al. | | |
| 8,323,007 | B2 * | 12/2012 | Butterfield | ........ | A61M 5/14224 417/413.1 |
| 8,616,862 | B2 | 12/2013 | Meza et al. | | |
| 9,482,218 | B2 * | 11/2016 | Coates | .................. | A61M 1/106 |
| 2001/0043450 | A1 * | 11/2001 | Seale | ........................ | F01L 9/04 361/160 |
| 2003/0194332 | A1 * | 10/2003 | Jahn | ..................... | F04B 43/0733 417/395 |
| 2004/0019313 | A1 * | 1/2004 | Childers | ............. | A61M 1/1696 604/5.01 |
| 2006/0110268 | A1 * | 5/2006 | De Koning | ........... | F04B 43/067 417/413.1 |
| 2007/0040454 | A1 * | 2/2007 | Freudenberger | ...... | F04B 17/042 310/12.04 |
| 2007/0189910 | A1 * | 8/2007 | Haeberle | ............. | F04B 43/0054 417/321 |
| 2007/0278155 | A1 * | 12/2007 | Lo | ........................ | A61M 1/3627 210/646 |
| 2010/0021313 | A1 * | 1/2010 | Devan | ..................... | F04B 17/03 417/44.1 |
| 2010/0022354 | A1 * | 1/2010 | Fisher | ................. | A63B 22/0605 482/8 |
| 2010/0316512 | A1 * | 12/2010 | Becker | .................. | F04B 45/043 417/413.1 |
| 2011/0020156 | A1 * | 1/2011 | Van Brunt | .............. | F04B 17/04 417/416 |
| 2011/0132190 | A1 * | 6/2011 | Koch | ...................... | F04B 3/003 92/169.3 |
| 2011/0274566 | A1 * | 11/2011 | Amirouche | ........ | A61M 5/14224 417/322 |
| 2013/0183170 | A1 * | 7/2013 | Laermer | .................. | F04B 43/02 417/313 |
| 2013/0315757 | A1 * | 11/2013 | Tsuboi | .................... | H01H 37/58 417/413.1 |
| 2013/0330208 | A1 * | 12/2013 | Ly | ......................... | F04B 17/042 417/45 |
| 2014/0018728 | A1 * | 1/2014 | Plahey | ..................... | A61M 1/16 604/29 |
| 2014/0161644 | A1 * | 6/2014 | Weatherley | ........... | F04B 43/021 417/360 |

\* cited by examiner

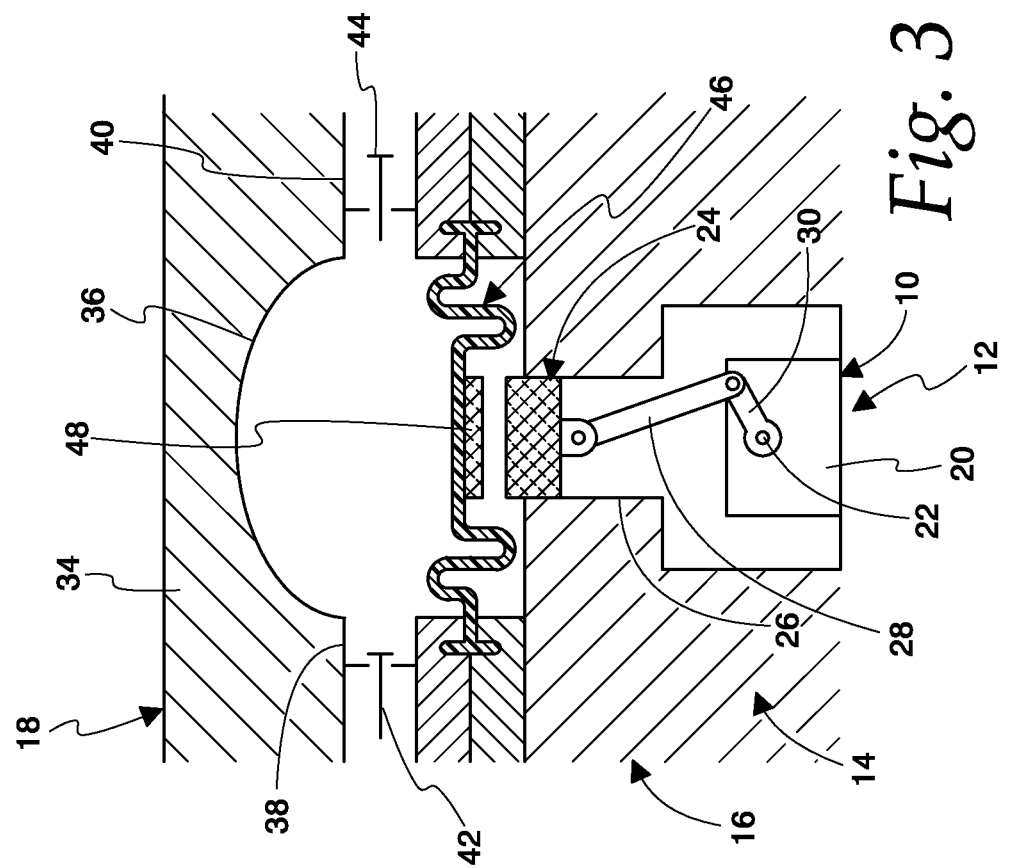
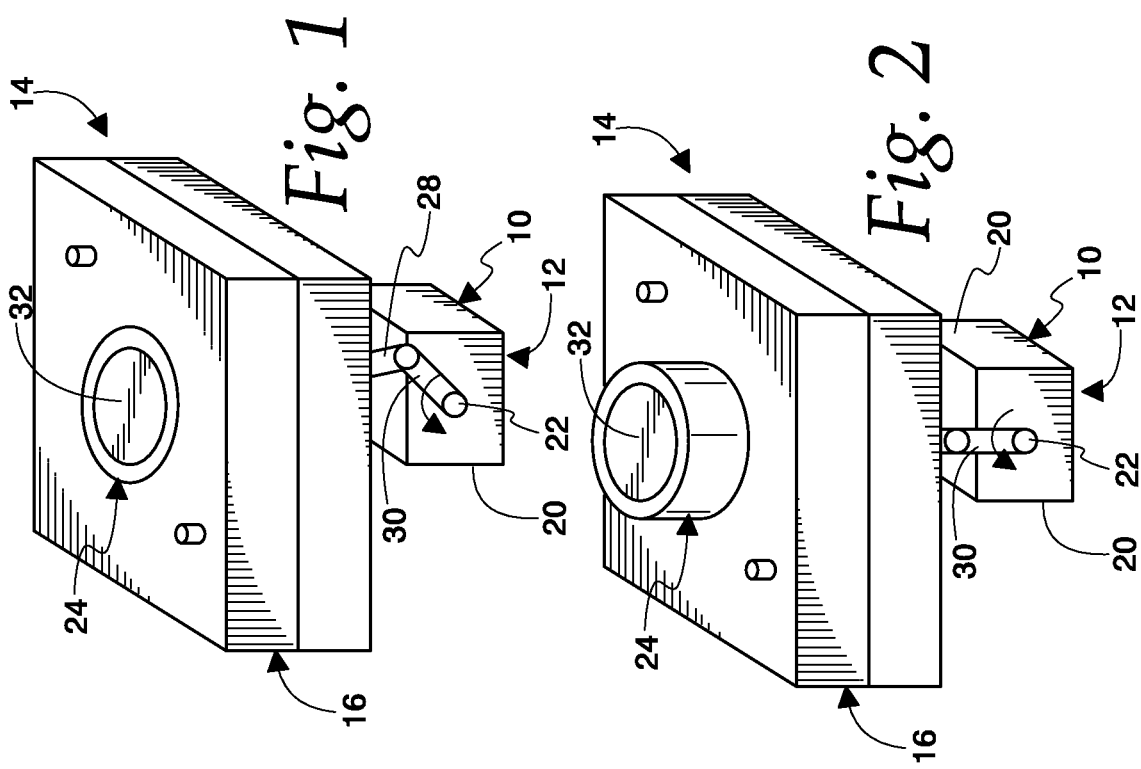

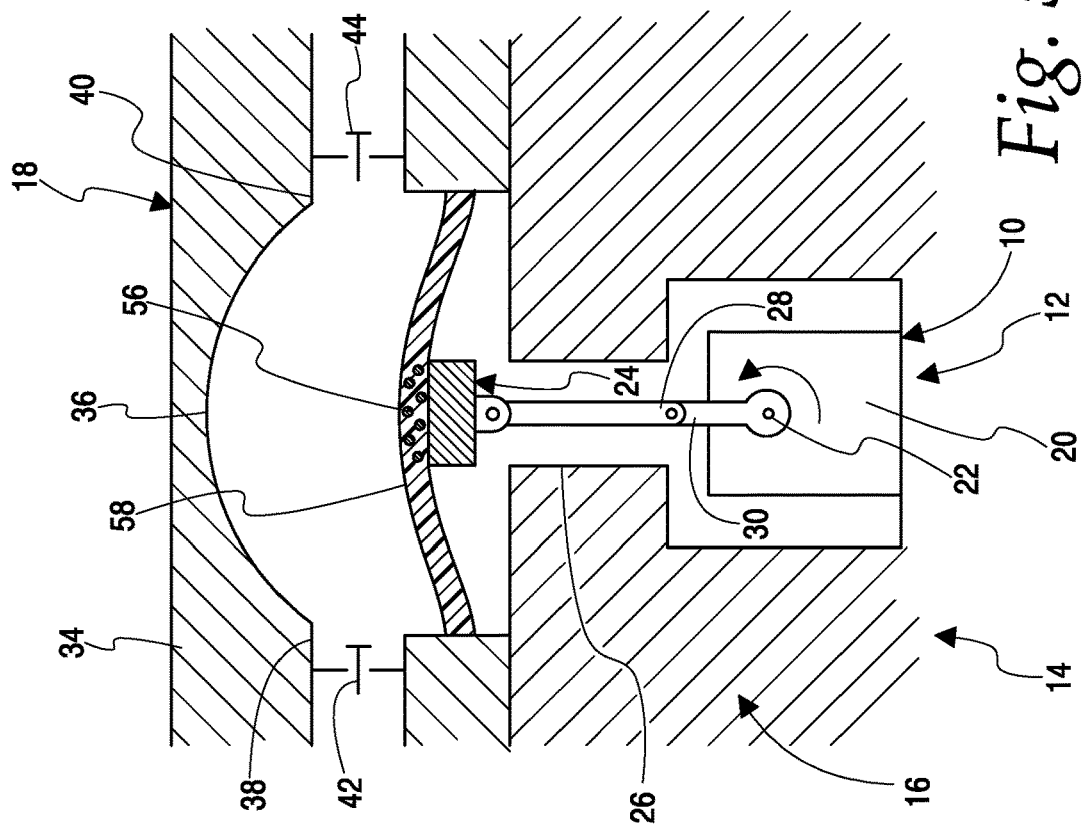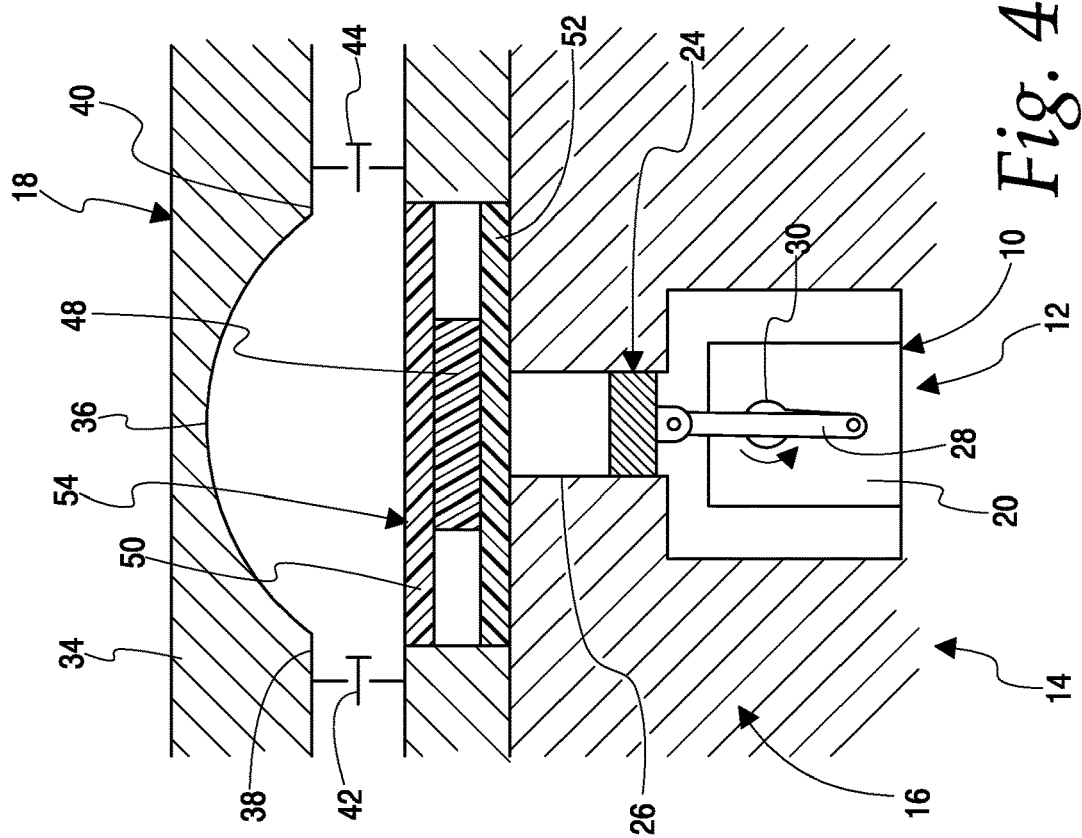

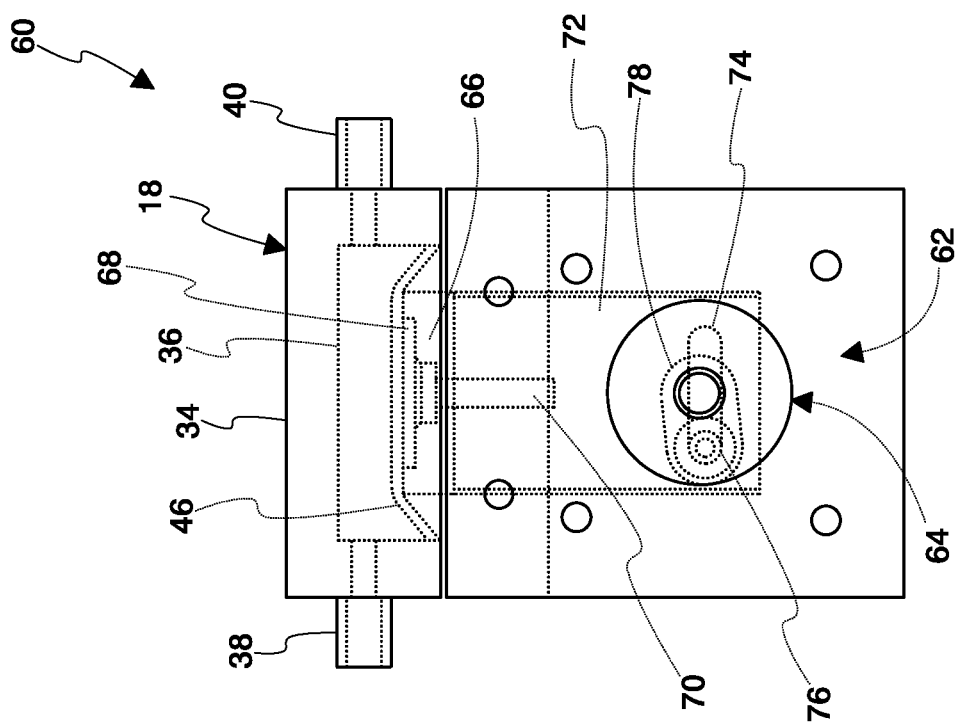
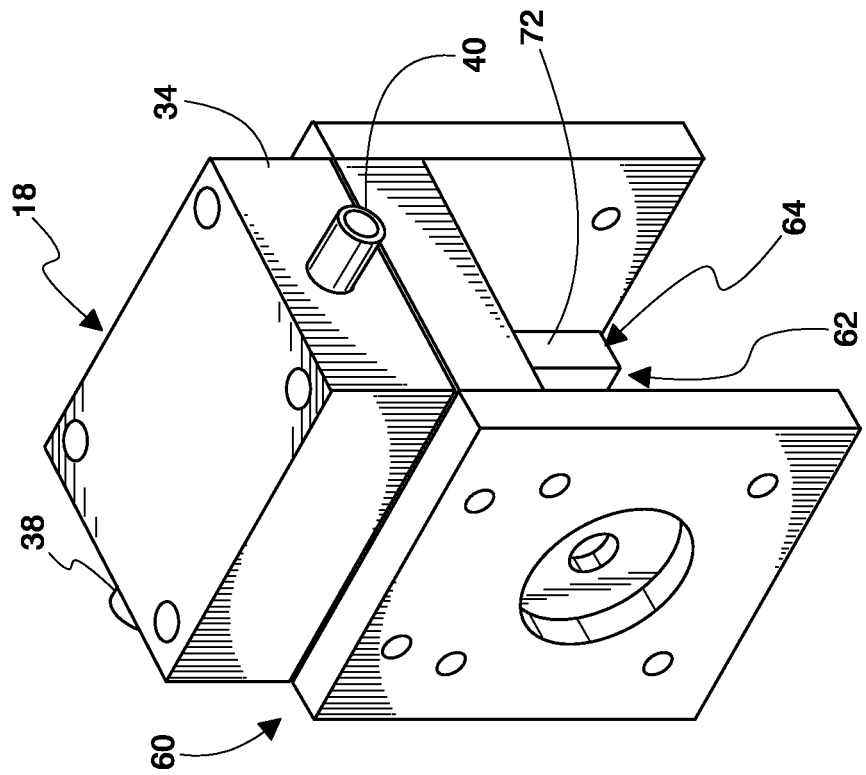

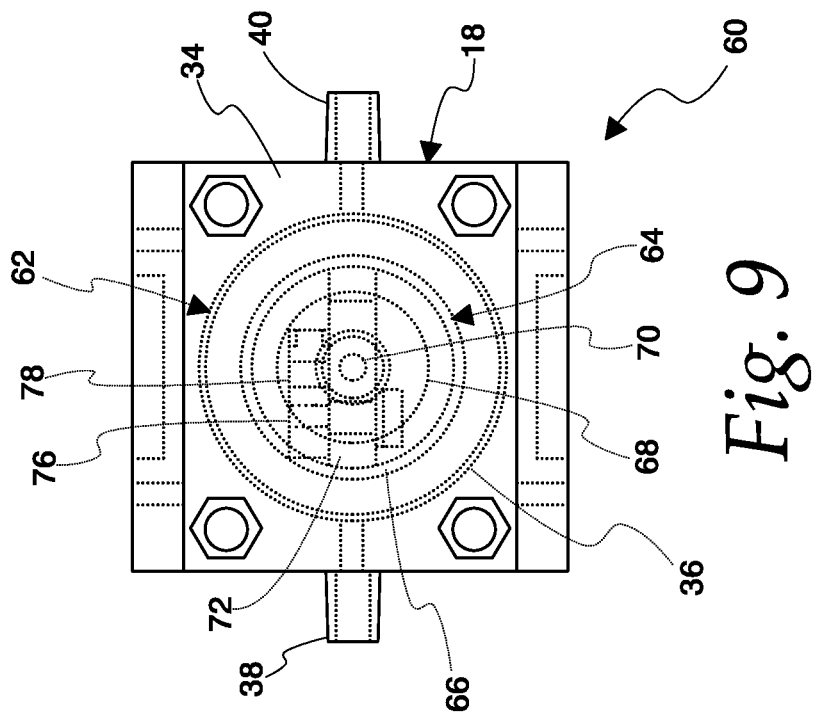
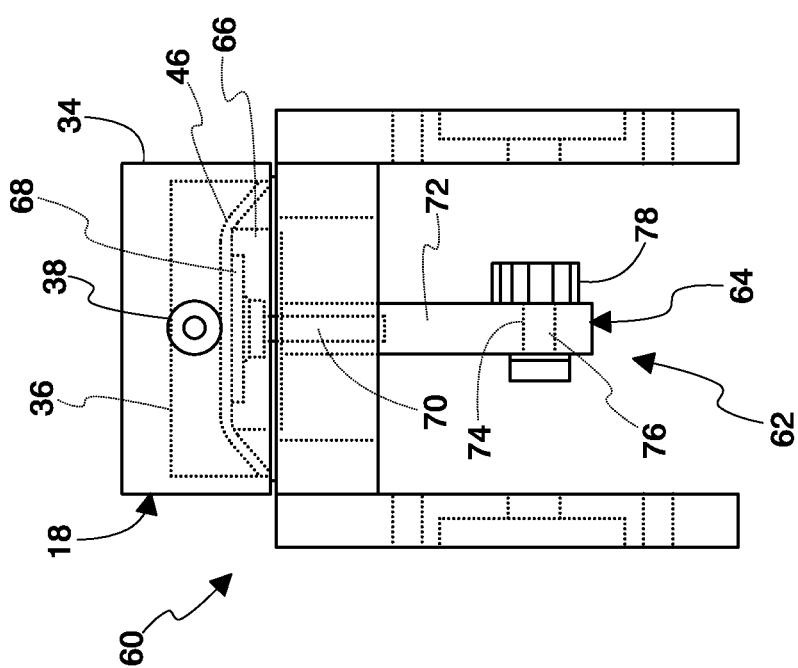

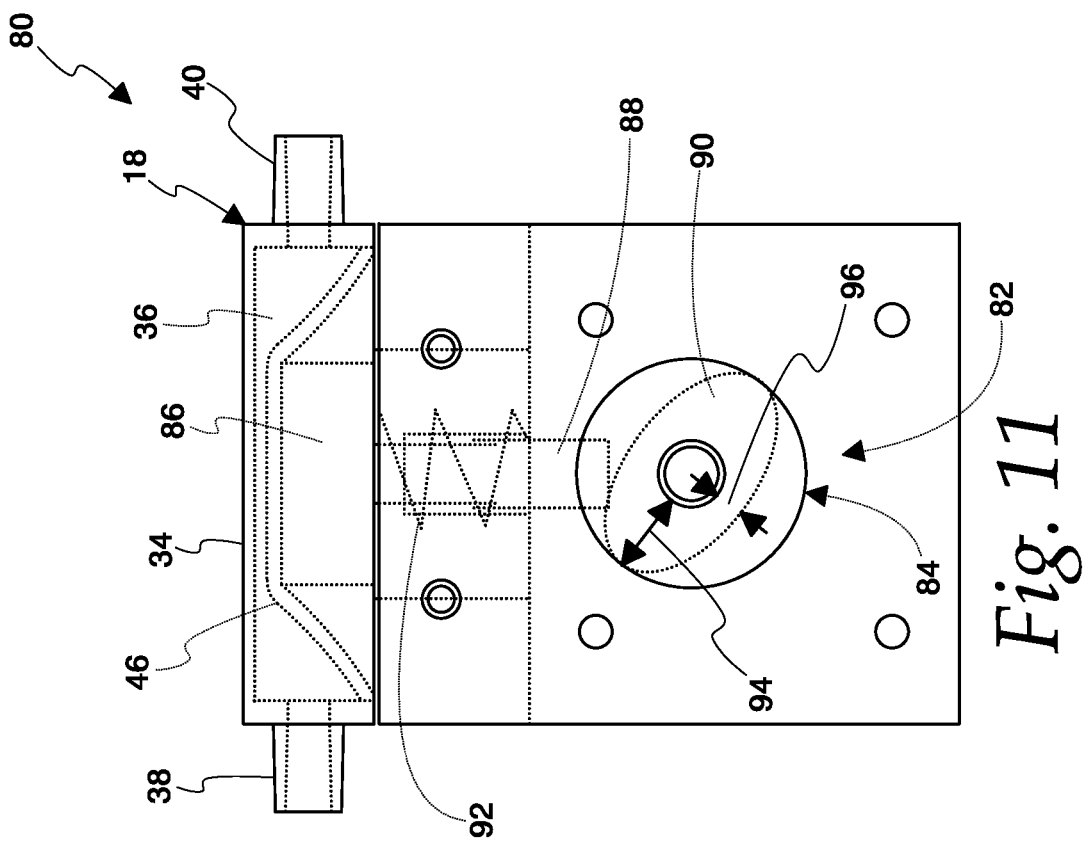
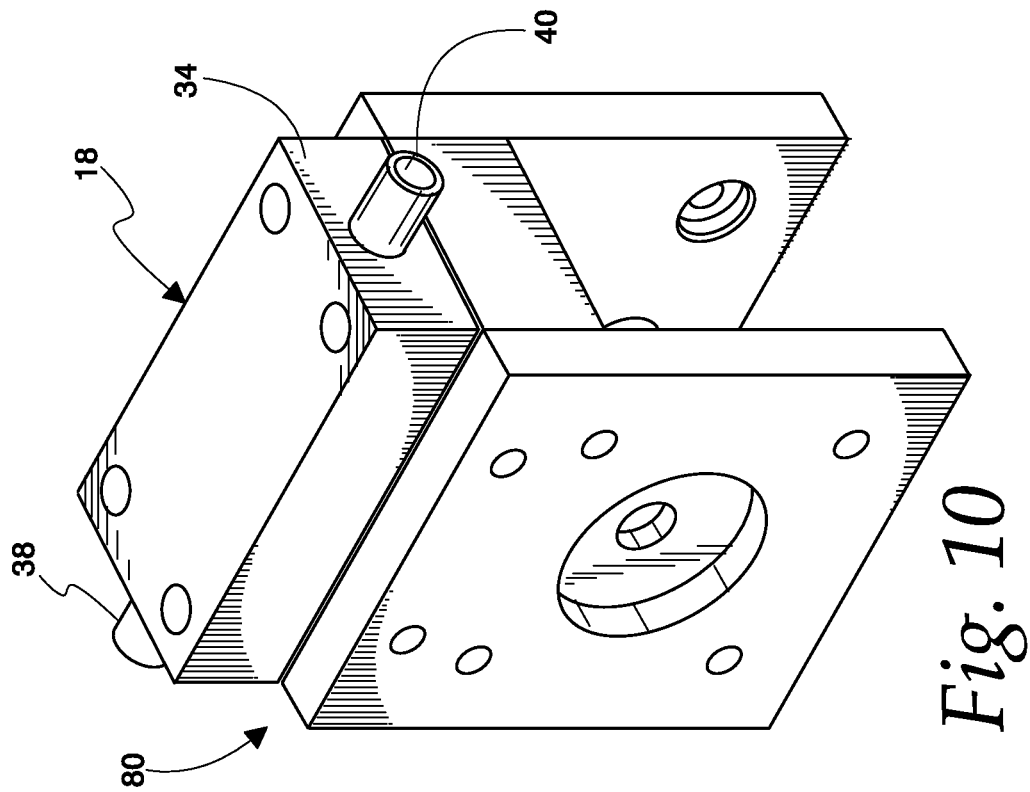
Fig. 11
Fig. 10

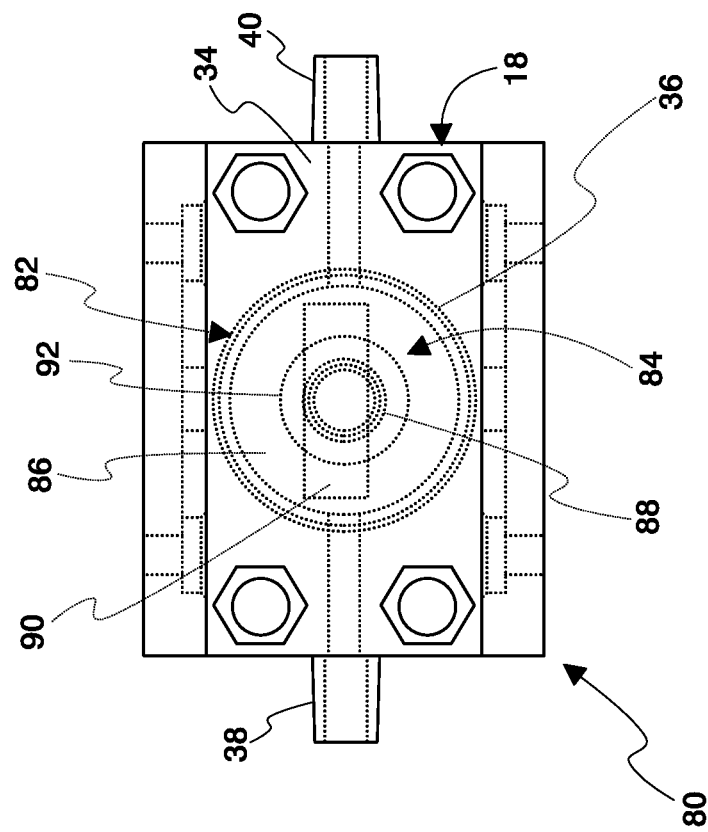
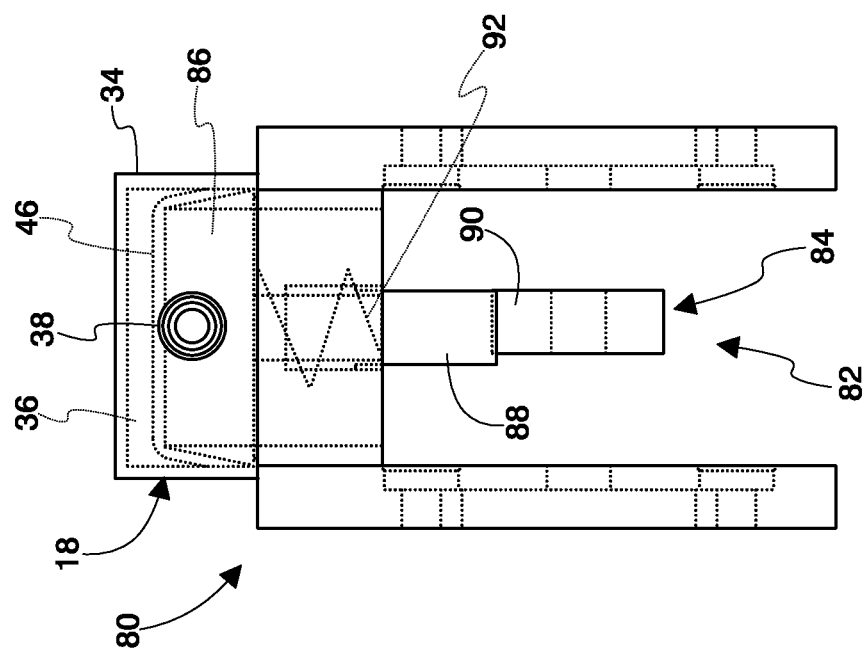

MAGNET-BASED SYSTEMS AND METHODS FOR TRANSFERRING FLUID

BACKGROUND

Field of the Disclosure

The present subject matter relates to systems and methods for moving fluid through a fluid circuit. More particularly, the present subject matter relates to systems and methods in which magnetism is used to assist in the control of fluid flow through a fluid circuit.

Description of Related Art

A variety of systems and methods are known for pumping or otherwise moving fluid through a fluid flow path, with the most preferable method for moving fluid through a fluid flow path depending on a number of factors. For example, extracorporeal processing of bodily fluid (e.g., blood withdrawal and separation or peritoneal dialysis) may involve any of a number of fluid movement techniques and devices. According to one approach, a durable processing system or device is used in combination with a disposable processing set or circuit. The durable processing system typically includes a pump assembly that interacts with one or more of the components of the disposable circuit to draw blood or another bodily fluid from a patient or donor or subject and then move the blood or bodily fluid to another location within the disposable circuit, which may include returning or all of portion of the blood or bodily fluid to the patient or donor or subject.

Frequently, the component of the disposable circuit that interacts with the pump assembly is a molded plastic piece commonly referred to as a cassette. As used herein, the term "cassette" refers to a component of a fluid processing system that includes one or more defined fluid passageways. The cassette is secured to a cassette holder or cassette station of the durable equipment, with a flexible membrane or diaphragm or sheet of the cassette facing the durable equipment. The cassette holder or cassette station typically includes a number of valve actuators that selectively press against the flexible diaphragm for opening and closing valve stations of the cassette, thereby controlling which of the fluid passageways are connected to each other and directing the fluid between any of a number of sources and destinations.

An exemplary cassette and cassette holder are employed by the AMICUS® system marketed by Fenwal, Inc. of Lake Zurich, Ill. One version of the AMICUS® system is described in greater detail in U.S. Pat. No. 5,868,696, which is hereby incorporated herein by reference. In the AMICUS® system, fluid flow is controlled by a disposable cassette with preformed fluid passages, which interfaces with an array of actuators and sensors located on a panel of the durable hardware. Flexible tubing loops connected to opposing edges of the cassette are received within peristaltic pump stations having rollers that press against the loops and rotate to move fluid through the cassette (and through the other components of the disposable circuit).

According to another cassette-based approach, the cassette holder includes both valve actuators and pump actuators, with the cassette defining not only valve stations, but also pump stations. Just as the valve actuators press against the valve stations to provide a valving function to the fluid passageways of the cassette, the pump actuators press against the diaphragm of the cassette at designated pump stations to provide a pumping function that moves fluid through the fluid passageways. An exemplary cassette and processing system of this type are described in U.S. Pat. No. 5,989,423, which is hereby incorporated herein by reference.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid pump is provided for use in combination with a fluid processing cassette having a flexible diaphragm. The fluid pump includes a motor and a piston movable toward and away from the flexible diaphragm of the fluid processing cassette. A linkage connects the motor and the piston, with the motor functioning to move the piston toward and away from the flexible diaphragm of the fluid processing cassette. At least a portion of the piston or the diaphragm is magnetized and at least a portion of the other is magnetized or formed of a ferromagnetic material so as to magnetically couple the piston and the flexible diaphragm.

In another aspect, a fluid processing system includes a cassette and a fluid transfer assembly. The cassette defines a fluid flow path defined at least in part by a pump cavity in fluid communication with at least two ports, with a flexible diaphragm being associated with the pump cavity for isolating the ports from the outside environment. The fluid transfer assembly includes a fluid pump with a motor and a piston movable toward and away from the flexible diaphragm of the cassette. A linkage connects the motor and the piston, with the motor functioning to move the piston toward and away from the flexible diaphragm. At least a portion of the piston or the flexible diaphragm is magnetized and at least a portion of the other is magnetized or formed of a ferromagnetic material so as to magnetically couple the piston and the flexible diaphragm.

In yet another aspect, a method is provided for transferring fluid through a fluid flow path. The method includes providing a fluid flow path defined at least in part by a pump cavity including at least two ports and an associated flexible diaphragm that isolates the ports from the outside environment. The method further includes moving the flexible diaphragm toward and/or away from the pump cavity to change the effective volume of the pump cavity, thereby drawing fluid into or forcing fluid out of the pump cavity via at least one of the ports, with the flexible diaphragm being moved at least in part under the force of magnetism.

In yet another aspect, a valve actuator is provided for use in combination with a fluid processing cassette having a flexible diaphragm. The valve actuator includes an actuator head that is movable toward and away from the flexible diaphragm of the fluid processing cassette. At least a portion of the actuator head or the diaphragm is magnetized and at least a portion of the other is magnetized or formed of a ferromagnetic material so as to magnetically couple the actuator head and the flexible diaphragm, thereby causing the diaphragm of the cassette to be moved at least in part under the force of magnetism.

BRIEF DESCRIPTION OF THE DRAWINGS

FIG. 1 is a perspective view of an exemplary fluid pump of a fluid transfer assembly of a fluid processing system according to an aspect of the present disclosure, with a piston of the fluid pump in a partially deployed position;

FIG. 2 is a perspective view of the fluid pump of FIG. 2, with a piston of the fluid pump in a deployed position;

FIG. 3 is a cross-sectional view of the fluid pump of FIG. 1, with a fluid processing cassette of a disposable set or circuit in operative engagement with the fluid pump;

FIG. 4 is a cross-sectional view of the fluid pump of FIG. 1, with an alternative embodiment of a fluid processing cassette in operative engagement with the fluid pump;

FIG. 5 is a cross-sectional view of the fluid pump of FIG. 1, with another alternative embodiment of a fluid processing cassette in operative engagement with the fluid pump;

FIG. 6 is a perspective view of another embodiment of a fluid pump of a fluid transfer assembly of a fluid processing system according to an aspect of the present disclosure, shown with a pump station of a fluid processing cassette of a disposable set or circuit in operative engagement with the fluid pump;

FIG. 7 is a front elevational view of the fluid pump and pump station of FIG. 6;

FIG. 8 is a side elevational view of the fluid pump and pump station of FIG. 6;

FIG. 9 is a top plan view of the fluid pump and pump station of FIG. 6;

FIG. 10 is a perspective view of another embodiment of a fluid pump of a fluid transfer assembly of a fluid processing system according to an aspect of the present disclosure, shown with a pump station of a fluid processing cassette of a disposable set or circuit in operative engagement with the fluid pump;

FIG. 11 is a front elevational view of the fluid pump and pump station of FIG. 10;

FIG. 12 is a side elevational view of the fluid pump and pump station of FIG. 10;

FIG. 13 is a top plan view of the fluid pump and pump station of FIG. 10;

DESCRIPTION OF THE ILLUSTRATED EMBODIMENTS

Figure 14:
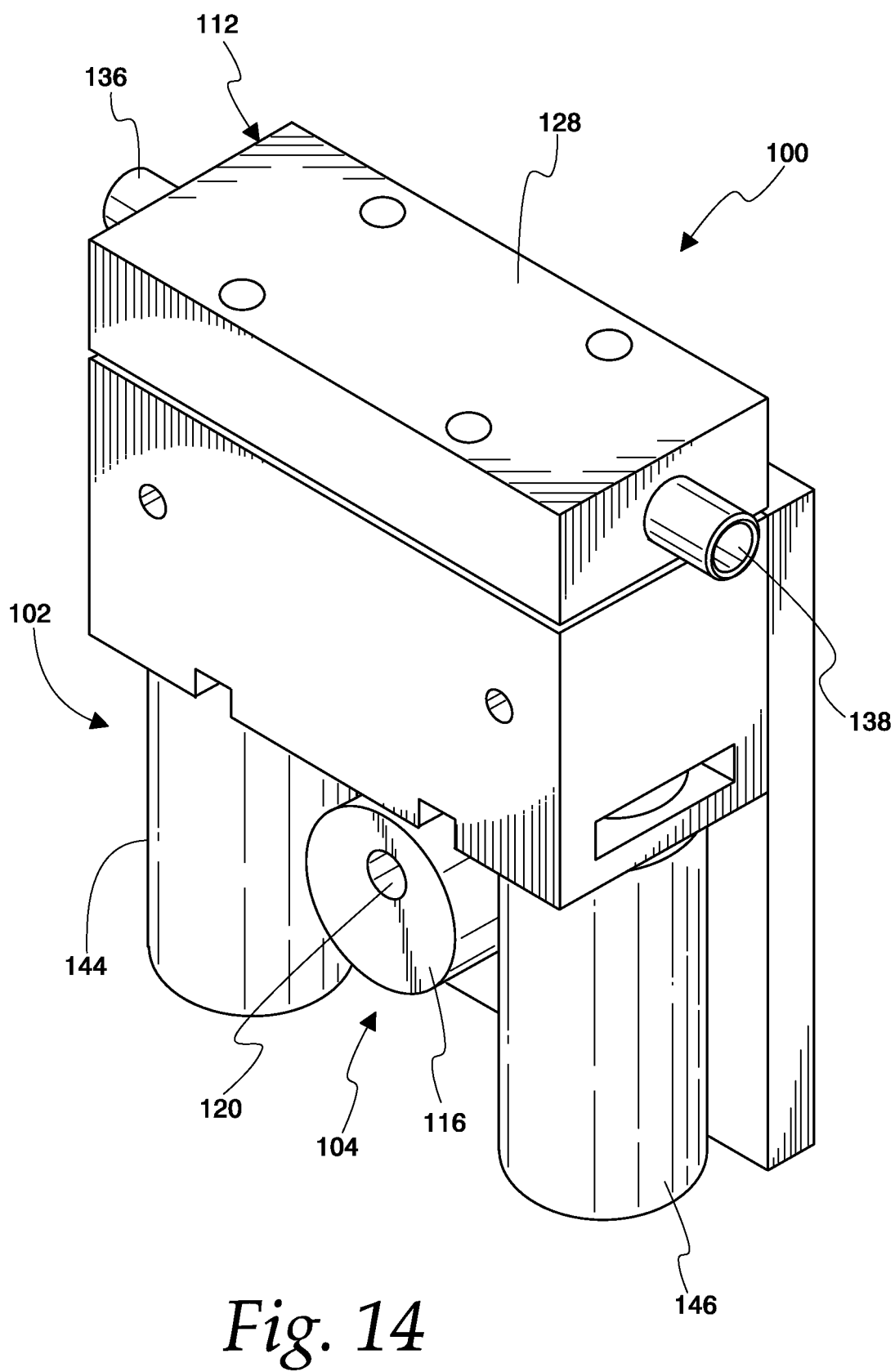
FIG. 14 is a perspective view of another embodiment of a fluid pump of a fluid transfer assembly of a fluid processing system according to an aspect of the present disclosure, shown with a pump station of a fluid processing cassette of a disposable set or circuit in operative engagement with the fluid pump.

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

FIGS. 1-5 show a fluid pump 10 of a fluid transfer assembly 12 of a durable fluid processing system 14. In one embodiment, the fluid processing system 14 is suitable for drawing blood or a bodily fluid from a patient or donor or subject or a non-living source (e.g., a storage bag), processing the fluid (e.g., separating it into two or more constituents), and then storing the fluid, disposing of the fluid, and/or returning the fluid to the source. In other embodiments, the fluid processing system 14 may be provided for use in transferring non-bodily fluid through a fluid circuit.

The fluid processing system 14 includes a surface or station 16 that may be accessed to place a separate fluid processing cassette 18 (FIG. 3) into operative engagement with the fluid pump 10 and the fluid transfer assembly 12. The surface or station 16 may be referred to as a "cassette holder" and take any of a number of forms, such as a horizontal or inclined surface or panel onto which a cassette 18 may be placed and then held in place by clamps or clips or the like. In other embodiments, the cassette holder may be a vertical surface with a door or cover hingedly attached thereto. The door may be opened to place a cassette against the vertical surface, with the door then being closed to hold the cassette in place against the vertical surface. Any of a number of other configurations of a cassette holder are also possible and within the scope of the present disclosure.

FIGS. 1-5 illustrate a cassette holder 16 with a single fluid pump 10 associated therewith, but it should be understood that a single cassette holder may include more than one fluid pump, as well as a number of other components. For example, in one embodiment, a cassette holder may include a number of fluid pumps (either similarly or differently configured) for interacting with a fluid processing cassette to move fluid through a fluid flow path defined by the cassette, a number of valve actuators for interacting with a cassette for changing the path of fluid moving through the fluid flow path, and one or more sensors for sensing pressure within the cassette or some other parameter. The exact configuration of the cassette holder depends on the configuration of the associated cassette, as the two are configured to form a matched pair, with the number and location of the fluid pumps of the cassette holder corresponding to the number and location of pump stations of the cassette, the number and location of the valve actuators of the cassette holder corresponding to the number and location of the valve stations of the cassette, and so on.

The fluid pump 10 of FIGS. 1-5 includes a motor 20 which rotates a driveshaft 22. A linkage associates the driveshaft 22 to a piston 24 of the fluid pump 10 to cause the piston 24 to move through a piston chamber 26 defined by the cassette holder 16 (FIGS. 3-5). The operation of the motor 20 causes the piston 24 to move between a down or retracted position (FIG. 4) and an up or deployed position (FIGS. 2 and 5), with the piston 24 passing through intermediate or partially deployed positions (e.g., FIGS. 1 and 3) between the retracted and deployed positions. The piston 24 is also movable between the retracted position and a partially deployed position or between the deployed position and a partially deployed position or between two partially deployed positions, depending on how the motor 20 is operated.

In the illustrated orientation, the vertical location of the piston 24 determines its position within the piston chamber 26. Thus, when the piston 24 is at its highest vertical position (FIG. 5), it is considered to be in its deployed position. On the other hand, the piston 24 may be considered to be in its retracted position when it is at its lowest vertical position (FIG. 4). It should be understood that the fluid pump orientation shown in FIGS. 1-5 (and the other fluid pumps illustrated herein) is merely exemplary, and the fluid pump 10 may be oriented upside down (i.e., with the motor 20 positioned vertically above the piston 24) or horizontally (i.e., with the motor 20 positioned at the same general vertical position as the piston 24) or on an incline. Hence, the references to the vertical location of the piston 24 as defining its degree of deployment arise from the illustrated orientation, and it should be understood that, in other embodiments, some other relative coordinate system may be more appropriate to describe the degree of deployment of the piston 24 (e.g., the horizontal location of the piston 24 is determinative of its degree of deployment if the illustrated fluid pump 10 were rotated 90° to place it on its side).

In the illustrated embodiment, the driveshaft 22 is rotated by the motor 20 to move only a single piston 24 of a fluid pump 10, but it is also within the scope of the present disclosure for the motor to include an elongated driveshaft that is associated with linkages of one or more additional fluid pumps to move the pistons of one or more other fluid pumps. Alternatively, if the fluid transfer assembly 12 includes a plurality of fluid pumps, separate motors may be provided for each fluid pump, which may be preferred if the movement of the pistons of the various fluid pumps is to be asynchronous.

In the illustrated embodiment, the upper or outer surface of the piston 24 is positioned within the piston chamber 26 when the piston 24 is in the retracted position (FIG. 4) and positioned above the outer surface of the cassette holder 16 (i.e., outside of the piston chamber 26) when the piston 24 is in the deployed position (FIGS. 2 and 5). In another embodiment, the upper or outer surface of the piston 24 may be positioned within the piston chamber 26 when the piston 24 is in the retracted position (FIG. 4) and positioned substantially flush with the outer surface of the cassette holder 16 or positioned at a lesser depth within the piston chamber 26 (i.e., farther from the motor 20) when the piston 24 is in the deployed position. In yet another embodiment, the outer surface of the piston 24 may be substantially flush with the outer surface of the cassette holder 16 when the piston 24 is in the retracted position and positioned above the outer surface of the cassette holder 16 (i.e., outside of the piston chamber 26) when the piston 24 is in the deployed position (FIG. 2). In yet another embodiment, the upper or outer surface of the piston 24 may be positioned outside of the piston chamber 26 in the retracted position and positioned farther outside of the piston chamber 26 (i.e., farther from the motor 20) in a deployed position.

The linkage that translates the rotational motion of the motor driveshaft 22 into translational movement of the piston 24 may take any of a number of forms. In the embodiment of FIGS. 1-5, the linkage includes a connecting rod 28 pivotally connected to the piston 24 (e.g., to a lower surface or underside of the piston 24), with the connecting rod 28 also being pivotally connected to a crankshaft 30. The crankshaft 30 is connected to the driveshaft 22 of the motor 20 and rotates with the driveshaft 22 as the driveshaft 22 is rotated by the motor 20, as shown in FIGS. 1-5. The angular orientation of the crankshaft 30 determines the location of the piston 24. In the orientation of FIGS. 1-5, the piston 24 will be in a deployed position (FIGS. 2 and 5) when the crankshaft 30 is oriented vertically upwardly (i.e., at 12:00), whereas the piston 24 will be in the retracted position (FIG. 4) when the crankshaft 30 is oriented vertically downwardly (i.e., at 6:00). When the crankshaft 30 is positioned at any other angular orientation (e.g., FIGS. 1 and 3), the piston 24 will be in a partially deployed position.

In the illustrated embodiment, the motor 20 rotates the driveshaft 22 in one direction, which is shown as a counterclockwise direction, but it is also within the scope of the present disclosure for the motor 20 to rotate the driveshaft 22 in a clockwise direction. When the motor 20 is run in one direction, it causes the piston 24 to move through the piston chamber 26 with a reciprocating motion, cyclically moving between the retracted and deployed positions. In other embodiments, the motor 20 may be driven in a different pattern, such as rotating a quarter turn in one direction and then a quarter turn in the other direction and so on, resulting in different movement patterns of the piston 24 (including a pattern in which the extent of the movement of the piston 24 is between two different intermediate or partially deployed positions).

The various components of the fluid pump 10 may be manufactured of any suitable material without departing from the scope of the present disclosure. For example, the piston 24 (or a portion thereof) may be formed of a metallic material or a plastic material or an elastomeric material or some other (preferably durable) material. According to an aspect of the present disclosure, at least a portion 32 of the piston 24 is magnetized or formed of a ferromagnetic material (FIGS. 1 and 2). When used herein, the term "magnetized" or "magnetic" refers to either a substance or component that generates a magnetic field (e.g., a permanent magnet), while the term "ferromagnetic" refers to a material or substance or component that is attracted to a magnet when within the magnetic field generated by a magnetized member. The exact material composition of the magnetized or ferromagnetic portion 32 of the piston 24 may vary without departing from the scope of the present disclosure, being formed of iron or some other magnetizable substance or substances. It may be advantageous for all or a portion of the outer or upper surface of the piston 24 (i.e., the surface facing away from the motor 20) to be magnetized or formed of a ferromagnetic material (as in the illustrated embodiment), but it is also within the scope of the present disclosure for some other portion or portions of the piston 24 to be magnetized or formed of a ferromagnetic material. The advantages of a piston 24 having a magnetized or ferromagnetic portion 32 will be described in greater detail herein.

If the piston 24 includes a magnetized, rather than ferromagnetic portion 32, it may be preferred for the other components of the fluid transfer assembly 12, including the portion of the cassette holder 16 defining the piston chamber 26, to be configured so as to be unaffected by the magnetized portion or portions 32 of the piston 24. For example, the cassette holder 16 (or at least the portion defining the piston chamber 26) may be formed of a plastic material that is neither attracted to nor repelled by a magnet in its presence. By such a configuration, the at least partially magnetized piston 24 may be moved through the piston chamber 26 without being attracted to or repelled by the piston chamber 26, thereby rendering the operation of the piston 24 more predictable; however, it is also within the scope of the present disclosure for the piston chamber 26 and/or the other portions of the fluid transfer assembly 12 to be attracted to or repelled by the at least partially magnetized piston 24.

As shown in FIGS. 3-5, the fluid pump 10 is configured for use in combination with a fluid processing cassette 18 of a (preferably disposable) fluid flow set or circuit. The cassette 18 may be variously configured without departing from the scope of the present disclosure but, in one embodiment, includes a relatively rigid (e.g., injection molded) body 34 that defines a fluid flow path. The fluid flow path includes at least one cavity 36 defined by the body 34 of the cassette 18, with the cavity 36 including at least two ports 38 and 40. The ports 38 and 40 are shown as being positioned on opposing sides of the cavity 36, but it is within the scope of the present disclosure for the ports 38 and 40 to be differently positioned, oriented, and/or configured without departing from the scope of the present disclosure.

In the illustrated embodiment, each port 38, 40 includes an associated valve 42, 44 (e.g., a one-way valve) that selectively prevents and allows fluid flow through the associated port 38, 40 in either one direction or both directions. In the illustrated embodiment, the valves 42 and 44 are passive check valves that open and close based on pressure within the cavity 36 (as will be described in greater detail herein), but it is also within the scope of the present disclosure for active clamping elements to be incorporated into one or more of the ports of a cavity, as will be described in greater detail herein with respect to the embodiment of FIGS. 14-18. If active clamping elements are employed, it is possible to associate them with the motor, with one clamping element being automatically opened at a particular motor state (which corresponds to the deployed position of the piston, for example) and another clamping element being automatically opened at a different motor state (which corresponds to the retracted position of the piston, for example). Different valve or clamp elements may be selected for the ports, depending on whether unidirectional or bidirectional flow through the fluid flow path defined by the cassette is preferred, as well as other factors.

A flexible diaphragm 46 (FIG. 3) is associated with and overlies the cavity 36 to isolate the cavity 36 and the ports 38 and 40 from the outside environment. The diaphragm 46 may be secured to the cassette body 34 by any suitable means (e.g., by an ultrasonic weld or by pressure applied by contact between the cassette 18 and the cassette holder 16) to provide a fluid-tight seal. The combination of the cavity 36, the ports 38 and 40, and the diaphragm 46 may be referred to herein as a pump station of the cassette 18. While only one pump station is shown in the illustrated embodiment, it is within the scope of the present disclosure for the cassette to include a plurality of pump stations. If the cassette includes a number of cavities, then a single diaphragm may be provided to overlay all of the cavities, with the diaphragm being sealed around each cavity. Alternatively, each cavity may include its own associated diaphragm overlaying the cavity and sealed around the cavity. In yet another embodiment, two or more cavities of a cassette may share the same diaphragm (with the diaphragm being sealed around each cavity), while one or more other cavities may share the same second diaphragm (which is sealed around each of the associated cavities) or there may be separate diaphragms associated with each of these other cavities.

In addition to defining cavities that are incorporated into pump stations, the cassette body 34 may define other cavities or formations that cooperate with the diaphragm 46 (or a different diaphragm) and the fluid processing system 14 to provide other functions. For example, the cassette body 34 may define one or more cavities that form part of a fluid flow path, but provide a valving or fluid-directing function (when combined with a valve actuator of the fluid processing system 14) instead of a pumping function. The cassette body 34 may also or alternatively define one or more cavities that form part of the fluid flow path, but provide a pressure sensing function (when combined with a pressure sensor of the fluid processing system 14) instead of a pumping or valving function. It is also within the scope of the present disclosure for a single cavity or formation defined by the cassette body 34 to provide more than one function, such as providing both pumping and valving functions or both pumping and sensing functions.

The material composition of the cassette body 34 and the diaphragm 46 may vary without departing from the scope of the present disclosure. In one embodiment, in which the cassette 18 is used for processing bodily fluid, the cassette body 34 is made of a rigid medical grade plastic material, with the diaphragm 46 being made of a flexible sheet of medical grade plastic (e.g., polyvinyl chloride or silicone). In other embodiments, in which the cassette 18 is intended for processing non-bodily fluid, the cassette body 34 may be made of a non-medical grade rigid material (e.g., a rigid plastic material), with the diaphragm 46 being made of a non-medical grade flexible material (e.g., a sheet of flexible plastic material).

With the cassette 18 positioned against the cassette holder 16 so as to align the cavity 36 with the fluid pump 10, movement of the piston 24 away from the motor 20 and into contact with the diaphragm 46 will, upon further advancement of the piston 24, press the diaphragm 46 into the cavity 36 (FIG. 5). Pressing the diaphragm 46 into the cavity 36 decreases the effective volume of the cavity 36 and increases the pressure within the cavity 36. Increased pressure within the cavity 36 opens at least one of the port valves and forces all or a portion of the fluid within the cavity 36 out of the cavity 36 via the port having the open valve. In the illustrated embodiment, the valve 44 associated with the right port 40 (FIGS. 3-5) is configured to open when the pressure within the cavity 36 reaches a high enough level, whereas increased pressure in the cavity 36 causes the valve 42 associated with the left port 38 to remain closed. Hence, an upstroke of the piston 24 presses the diaphragm 46 into the cavity 36, opens the valve 44 of the right port 40, and forces any or a portion of the fluid within the cavity 36 out of the cavity 36 via the right port 40.

Movement of the piston 24 toward the motor 20 allows the diaphragm 46 to flex out of the cavity 36, returning to an initial, unstressed or equilibrium position. This returns the cavity 36 to its initial volume and pressure and causes any open valves (the valve 40 associated with the right port 44 in the illustrated embodiment) to close. According to an aspect of the present disclosure, the diaphragm 46 includes a magnetized or ferromagnetic portion 48 (FIG. 3), which attracts or is attracted to the magnetized or ferromagnetic portion 32 of the piston 24. In one embodiment, only one of the diaphragm 46 and the piston 24 includes a magnetized portion, while the other includes a portion formed of a ferromagnetic material. In another embodiment, both of the diaphragm 46 and the piston 24 include magnetized portions that are attracted to each other. By providing the piston 24 or diaphragm 46 with a magnetized portion and the other with a portion that is either magnetized or formed of a ferromagnetic material, a downstroke of the piston 24 moves the piston 24 toward the motor 20 and pulls the diaphragm 46 away from the cavity 36 under the force of magnetism. If the magnetic attraction between the magnetized/ferromagnetic portions 32 and 48 of the piston 24 and the diaphragm 46 is sufficiently strong, then the piston 24 may pull the diaphragm 46 out of the cavity 36 to the point that the effective volume of the cavity 36 increases and the pressure decreases to a vacuum condition. A vacuum condition within the cavity 36 opens at least one of the port valves and draws fluid into the cavity 36 via the port having the open valve. In the illustrated embodiment, the valve 42 associated with the left port 38 (FIG. 3) is configured to open when the pressure within the cavity 36 decreases to a vacuum condition, whereas a vacuum condition in the cavity 36 causes the valve 44 associated with the right port 40 to remain closed. Hence, a downstroke of the piston 24 pulls the diaphragm 46 out of the cavity 36 (when there is sufficient magnetic attraction between the piston 24 and the diaphragm 46 and sufficient movement of the piston 24 away from the cassette 18), opens the valve 42 of the left port 38, and draws fluid from an upstream portion of the fluid flow path into the cavity 36 via the left port 38.

Based on the foregoing, it will be seen that repeated movement of the piston 24 between the retracted and deployed positions (or between the retracted position and a partially deployed position or between a partially deployed position and the deployed position or between two partially deployed positions) will advance fluid through the cavity 36. It may be advantageous to provide at least two fluid pumps that operate 180° out of phase with each other, with one being configured to expel fluid from the associated pump station of the cassette while the other is drawing fluid into the associated pump station, thereby providing substantially continuous, non-pulsatile flow of fluid through the fluid flow path defined by the cassette.

The nature of the magnetized/ferromagnetic portion of the diaphragm may vary without departing from the scope of the present disclosure. For example, in one embodiment, which is shown in FIG. 3, the diaphragm 46 includes at least one magnetized or ferromagnetic member 48 that is secured to the diaphragm 46. The magnetized or ferromagnetic member 48 may be provided as a disk or any other shape, although it may be preferred for the magnetized or ferromagnetic member 48 to have a size and shape that mirrors the size and shape of the outer or upper face or surface of the associated piston 24 of the fluid transfer assembly 12. In FIG. 3, the magnetized or ferromagnetic member 48 is shown as being secured to the diaphragm 46 at a location outside of the cavity 36, which may be advantageous because it prevents the magnetized or ferromagnetic member 48 from coming into contact with any fluid in the cavity 36. In other embodiments, the magnetized or ferromagnetic member 48 may be secured to the diaphragm 46 at a location within the cavity 36. The means by which the magnetized or ferromagnetic member 48 is secured to the diaphragm 46 may vary without departing from the scope of the present disclosure. For example, the magnetized or ferromagnetic member 48 may be secured to the diaphragm 46 by an adhesive or by a physical connector or by a friction fit between the magnetized or ferromagnetic member 48 and the diaphragm 46 or the like.

In another embodiment, which is shown in FIG. 4, at least one magnetized or ferromagnetic member 48 is positioned between two layers 50 and 52 of a flexible diaphragm 54. The layers 50 and 52 of the flexible diaphragm 54 may be substantially identical to each other and to the diaphragm 46 described above with respect to the embodiment of FIG. 3, but it is also within the scope of the present disclosure for the two layers 50 and 52 to be differently configured from each other and from the diaphragm 54 of FIG. 3. The layers 50 and 52 of the diaphragm 54 may be secured to the magnetized or ferromagnetic member 48 by any suitable means (including the means described above with respect to the embodiment of FIG. 3), and it is possible for the magnetized or ferromagnetic member 48 to be secured to one layer by one means and to the other layer by a different means. The layers 50 and 52 of the diaphragm 54 may be secured to each other or remain separated. In one embodiment, the layers 50 and 52 of the diaphragm 54 are secured together around the perimeter of the magnetized or ferromagnetic member 48, thereby holding the magnetized or ferromagnetic member 48 in place between the layers 50 and 52 without directly securing the magnetized or ferromagnetic member 48 to either layer 50, 52.

In yet another embodiment, which is shown in FIG. 5, a magnetized or ferromagnetic material 56 is incorporated into the flexible diaphragm 58. This may be accomplished in any of a number of ways, such as by forming the diaphragm 58 and then injecting, implanting, or otherwise impregnating at least a portion of the formed diaphragm 58 with the magnetized or ferromagnetic material 56 (e.g., a molten metal that hardens within the diaphragm 58). In another embodiment, the magnetized or ferromagnetic material 56 may be initially provided (e.g., as small pieces or particles of metal), with the diaphragm 58 being subsequently formed around the magnetized or ferromagnetic material 56. The magnetized or ferromagnetic material 56 may be positioned anywhere within the diaphragm 58, although it may be advantageous for the magnetized or ferromagnetic material 56 to be primarily located at a central location of the diaphragm 58 to better interact with the magnetized or ferromagnetic portion 32 of the piston 24 of the fluid pump 10.

Regardless of the exact configuration of the piston and the diaphragm, it is within the scope of the present disclosure for them to interact (or be "magnetically coupled") upon direct contact or without direct contact between the piston and the diaphragm. If the system is dependent upon direct contact between the piston and the diaphragm, then the magnetic attraction therebetween may be less than what may be required when the piston is configured to move the diaphragm without directly contacting it. In one embodiment, the diaphragm and piston are configured such that the resiliency of the flexible diaphragm eventually overcomes the magnetic attraction between the diaphragm and piston upon sufficient retraction or movement of the piston away from the diaphragm. Thus, the diaphragm is sufficiently flexible and the magnetic attraction between the diaphragm and the piston is sufficiently strong to allow the piston to pull the diaphragm away from the cassette cavity up to a certain point. The tendency of the diaphragm to return to its initial configuration increases as it is pulled by the piston until the resiliency of the diaphragm becomes greater than the magnetic attraction between the diaphragm, at which time the diaphragm becomes magnetically uncoupled from the piston and returns to its initial configuration. In such an embodiment, it may be advantageous for the piston to avoid moving into the fully retracted position during use, but to instead move to a partially deployed position that pulls the diaphragm away from the diaphragm without causing the diaphragm to become magnetically uncoupled. After use, the motor of the fluid pump may then be operated to move the piston to the retracted position, thereby magnetically uncoupling the diaphragm from the piston and allowing the cassette to be removed from the cassette holder.

FIGS. 6-9 illustrate a system 60 incorporating an alternative embodiment of a fluid transfer assembly 62 having a fluid pump 64. Similar to the fluid pump 10 of FIGS. 1-5, the fluid pump 64 of FIGS. 6-9 includes a motor having a driveshaft (both omitted to better show the other components of the fluid pump 64) and a piston 66 having a magnetized or ferromagnetic portion 68. The linkage between the motor driveshaft and the piston 66 in the embodiment of FIGS. 6-9 differs from the linkage of FIGS. 1-5. In particular, a connecting rod 70 extends from the piston 66 and is received within or otherwise secured to a slotted plate or member 72 (although it is also possible for the connecting rod 70 and the slotted plate 72 to be integrated into a single component). The slotted plate 72 includes a generally horizontal slot 74 (FIG. 7) that receives a peg or post or follower 76 (FIG. 8). The peg or post or follower 76 is secured to a crankshaft 78 (FIG. 7) that is connected to the driveshaft of the motor, with the crankshaft 78 rotating with the driveshaft as the driveshaft is rotated by the motor.

The angular orientation of the crankshaft 78 determines the location of the peg or post or follower 76, which controls the position of the piston 66. In particular, the peg or post or follower 76 is allowed to slide or translate laterally through the slot 74 of the slotted plate 72 as it (along with the crankshaft 78) is rotated about the motor driveshaft. As the peg or post or follower 76 is positioned within the (generally horizontal) slot 74 of the slotted plate 72, the slotted plate 72 (and, hence, the piston 66) is constrained to move vertically in step with the peg or post or follower 76. In the orientation of FIGS. 6-9, the peg or post or follower 76 will be in its highest vertical position when the crankshaft 78 is oriented vertically upwardly (i.e., at 12:00), which also places the slotted plate 72 and the piston 66 at their highest vertical position or deployed position. When the motor has rotated the crankshaft 78 and the peg or post or follower 76 to their lowest vertical position (i.e., at 6:00), the slotted plate 72 and the piston 66 will also be at their lowest vertical position or retracted position. When the crankshaft 78 and the peg or post or follower 76 are positioned at any other angular orientation (e.g., as in FIG. 7), the slotted plate 72 and the piston 66 will be in a partially deployed position. Thus, as described above with respect to the embodiment of FIGS. 1-5, the motor of the fluid pump 64 operates to move the piston 66 through the piston chamber of the cassette holder. Also in accordance with the above description of the embodiment of FIGS. 1-5, movement of the piston 66 functions to move the diaphragm 46 of a fluid processing cassette 18 associated with the fluid pump 64 into an out of a cavity 36 of the cassette 18 to move fluid through a fluid flow path of which the cavity 36 is a part, at least partially under the force of magnetism.

FIGS. 10-13 illustrate a system 80 incorporating another alternative embodiment of a fluid transfer assembly 82 and fluid pump 84 (FIGS. 11-12). Similar to the fluid pumps of FIGS. 1-9, the fluid pump 84 of FIGS. 10-13 includes a motor having a driveshaft (both omitted to better show the other components of the fluid pump 84) and a piston 86 having a magnetized or ferromagnetic portion. The linkage between the motor driveshaft and the piston 86 in the embodiment of FIGS. 10-13 differs from the linkages of FIGS. 1-9. In particular, a follower 88 extends from the piston 86 to contact a cam 90. In one embodiment, the fluid pump 84 may include a spring 92 or similar resilient element that biases the follower 88 into contact with the cam 90 (which may be advantageous if gravity tends to urge the follower 88 out of contact with the cam 90, such as if the cam 90 is positioned above the follower 88). The cam 90 is connected to the driveshaft of a motor (both omitted to better illustrate the other components of the fluid pump 84), with the cam 90 rotating with the driveshaft as the driveshaft is rotated by the motor.

The cam 90 has a non-uniform outer perimeter, which is illustrated in FIG. 11 as an oval, but may be differently shaped without departing from the scope of the present disclosure. The shape of the cam 90 and its angular orientation (which varies as the driveshaft is rotated by the motor) determines the position of the piston 86. In particular, the follower 88 remains in contact with the cam 90 as the cam 90 is rotated by the motor driveshaft. The length of the follower 88 does not change, meaning that the position of the piston 86 within the piston chamber varies based on the distance between the driveshaft and the location of the cam 90 that is contacted by the follower 88 (i.e., the distance in a vertical direction in the orientation of FIGS. 10-13). As the perimeter of the cam 90 is non-uniform, the distance between the driveshaft and the location of the cam 90 that is contacted by the follower 88 changes as the cam 90 is rotated.

The distance between the driveshaft and the location of the cam 90 that is contacted by the follower 88 will be greatest when the portion of the cam 90 having the greatest radius is positioned between the driveshaft and the follower 88 (i.e., when this portion of the cam 90 is positioned at 12:00 in the orientation of FIG. 11). In the illustrated embodiment, this portion of the cam 90 is illustrated in FIG. 11 at 94. When the motor has operated to place this portion 94 of the cam 90 between the driveshaft and the follower 88, the follower 88 (and, hence, the piston 86) will be at its highest vertical position, which corresponds to the deployed position of the piston 86.

In contrast, the distance between the driveshaft and the location of the cam 90 that is contacted by the follower 88 will be smallest when the portion of the cam 90 having the smallest radius is positioned between the driveshaft and the follower 88 (i.e., when this portion of the cam 90 is positioned at 12:00 in the orientation of FIG. 11). In the illustrated embodiment, this portion of the cam 90 is illustrated in FIG. 11 at 96. When the motor has operated to place this portion 96 of the cam 90 between the driveshaft and the follower 88, the follower 88 (and, hence, the piston 86) will be at its lowest vertical position, which corresponds to the retracted position of the piston 86. When a portion of the cam 90 having an intermediate radius is positioned between the driveshaft and the follower 88 (as in FIG. 11), the follower 88 and the piston 86 will be at an intermediate vertical position, which corresponds to a partially deployed position of the piston 86. Thus, as described above with respect to the embodiments of FIGS. 1-9, the motor of the fluid pump 84 operates to move the piston 86 through the piston chamber. Also in accordance with the above description of the embodiments of FIGS. 1-9, movement of the piston 86 functions to move the diaphragm 46 of a fluid processing cassette 18 associated with the fluid pump 84 into an out of a cavity 36 of the cassette 18 to move fluid through a fluid flow path of which the cavity 36 is a part, at least partially under the force of magnetism.

In the illustrated embodiment, the cam 90 is symmetrical, such that rotating the cam 90 180° from a given position will return the piston 86 to the same position it was in when the cam 90 was in the original position. In other embodiments, the cam may be non-symmetrical and irregularly shaped, allowing for a wide range of possible movement patterns for the piston 86, which affects the way in which fluid is moved through the cassette 18. Accordingly, a preferred fluid flow pattern may be customized by selecting a particularly shaped cam, as well as a particular motor operation profile (e.g., speed and direction of rotation).

FIGS. 14-18 illustrate a variation of the system 80 of FIGS. 10-13. The system 100 of FIGS. 14 and 15 employs a fluid transfer assembly 102 and fluid pump 104 (illustrated in greater detail in FIGS. 17 and 18) that are functionally similar to the fluid transfer assembly 82 and fluid pump 84 of FIG. 11, with a motor having a driveshaft (both omitted to better show the other components of the fluid pump 104) and a magnetized or ferromagnetic piston 106 (FIGS. 15 and 18) that interacts with magnetized or ferromagnetic material 108 of the flexible diaphragm 110 of a fluid processing cassette 112 in accordance with the foregoing description. The linkage between the motor driveshaft and the piston 106 in the embodiment of FIGS. 14-18 is provided as a follower 114, which extends from the piston 106 to contact a cam 116. In one embodiment, the fluid pump 104 may include a spring 118 or similar resilient element that biases the follower 114 into contact with the cam 116 (which may be advantageous if gravity tends to urge the follower 114 out of contact with the cam 116, such as if the cam 116 is positioned above the follower 114). The cam 116 is connected to the driveshaft of a motor (both omitted to better illustrate the other components of the fluid pump 104), with the cam 116 rotating with the driveshaft as the driveshaft is rotated by the motor.

Figure 15:
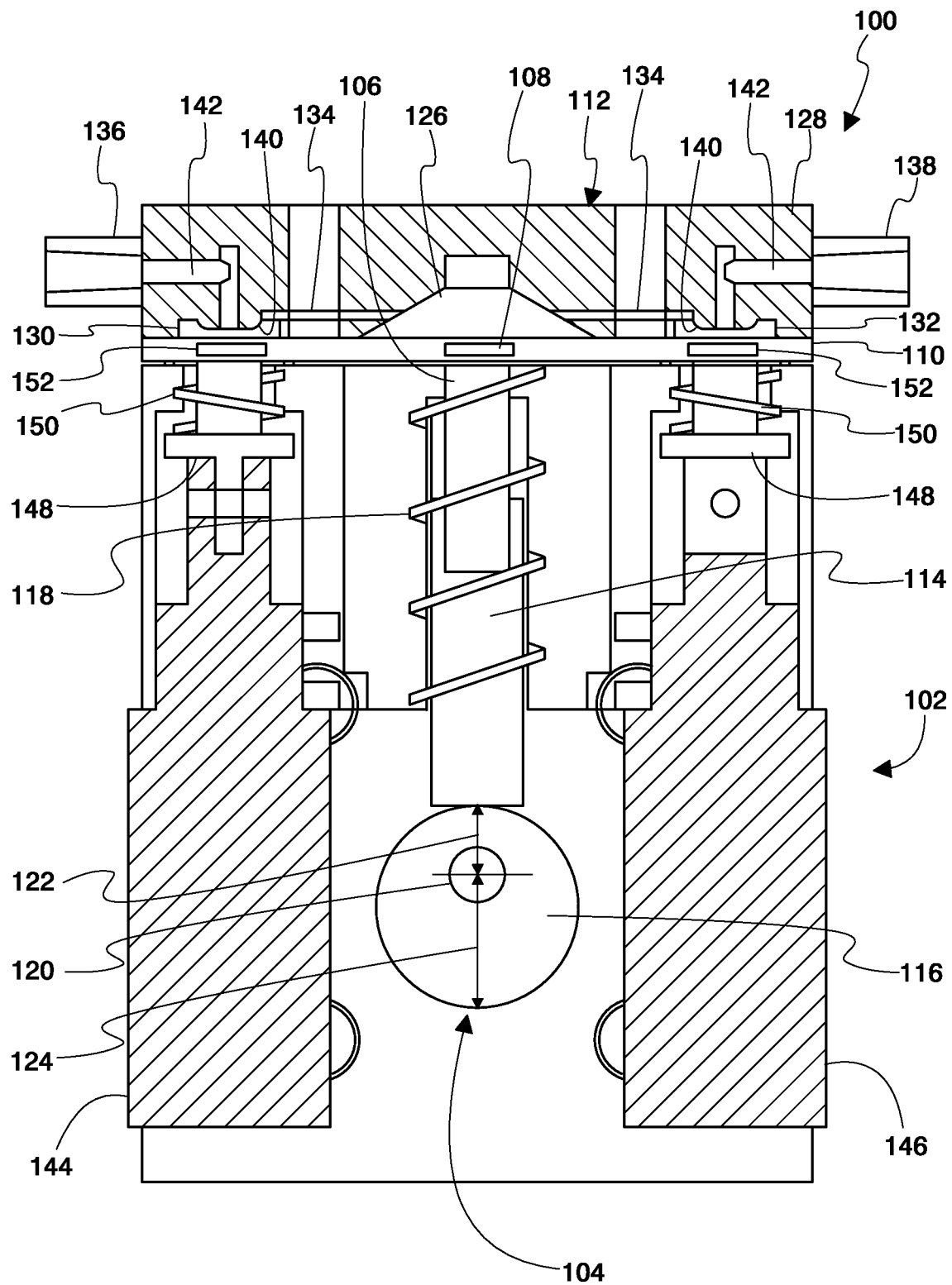
FIG. 15 is a cross-sectional view of the fluid pump and pump station of FIG. 14.

In contrast to the cam 90 of FIG. 11, the cam 116 of the embodiment of FIGS. 14-18 has a uniform, circular outer perimeter, which is best shown in FIG. 15, with an aperture 120 that is offset from the center of the cam 116 for receiving the driveshaft of the motor. The angular orientation of the cam 116 (which varies as the driveshaft is rotated by the motor) determines the position of the piston 106. In particular, the follower 114 remains in contact with the cam 116 as the cam 116 is rotated by the motor driveshaft about an axis defined by the aperture 120. The length of the follower 114 does not change, meaning that the position of the piston 106 within the piston chamber varies based on the distance between the driveshaft and the location of the cam 116 that is contacted by the follower 114 (i.e., the distance in a vertical direction in the orientation of FIG. 15). As the distance between the perimeter of the cam 116 and its rotation of axis is non-uniform, the distance between the driveshaft and the location of the cam 116 that is contacted by the follower 114 changes as the cam 116 is rotated.

The distance between the driveshaft and the location of the cam 116 that is contacted by the follower 114 will be smallest when the portion of the cam perimeter spaced closest to the aperture 120 is positioned between the driveshaft and the follower 114, as in the position of FIG. 15. In the illustrated embodiment, this portion of the cam 116 is illustrated in FIG. 15 at 122. When the motor has operated to place this portion 122 of the cam 116 between the driveshaft and the follower 114, the follower 114 (and, hence, the piston 106) will be at its lowest vertical position, which corresponds to the retracted position of the piston 106.

In contrast, the distance between the driveshaft and the location of the cam 116 that is contacted by the follower 114 will be greatest when the portion of the cam perimeter spaced farthest from the aperture 120 is positioned between the driveshaft and the follower 114 (i.e., when this portion of the cam 116 is positioned at 12:00 in the orientation of FIG. 15). In the illustrated embodiment, this portion of the cam 116 is illustrated in FIG. 15 at 124. When the motor has operated to place this portion 124 of the cam 116 between the driveshaft and the follower 114, the follower 114 (and, hence, the piston 106) will be at its highest vertical position, which corresponds to the deployed position of the piston 106. When a portion of the cam perimeter spaced an intermediate distance away from the aperture 120 is positioned between the driveshaft and the follower 114, the follower 114 and the piston 106 will be at an intermediate vertical position, which corresponds to a partially deployed position of the piston 106. Thus, as described above, the motor of the fluid pump 104 operates to move the piston 106 through the piston chamber. Also in accordance with the above description, movement of the piston 106 functions to move the diaphragm 110 of the fluid processing cassette 112 toward and away from a pump cavity 126 of the cassette 112 to move fluid through a fluid flow path of which the pump cavity 126 is a part, at least partially under the force of magnetism.

It will be seen that the cams 90 and 116 are differently configured, which may result in different movement profiles of the associated pistons 86, 106. The cam 90 of FIG. 11 may be incorporated into the fluid pump 104 of FIG. 15, while the cam 116 of FIG. 15 may be incorporated into the fluid pump 84 of FIG. 11. It is also within the scope of the present disclosure for a differently shaped cam to be incorporated into either fluid pump 84, 104. Additionally, various motor operation profiles may be employed to vary the movement profile of the associated pistons 86, 106.

Figure 16:
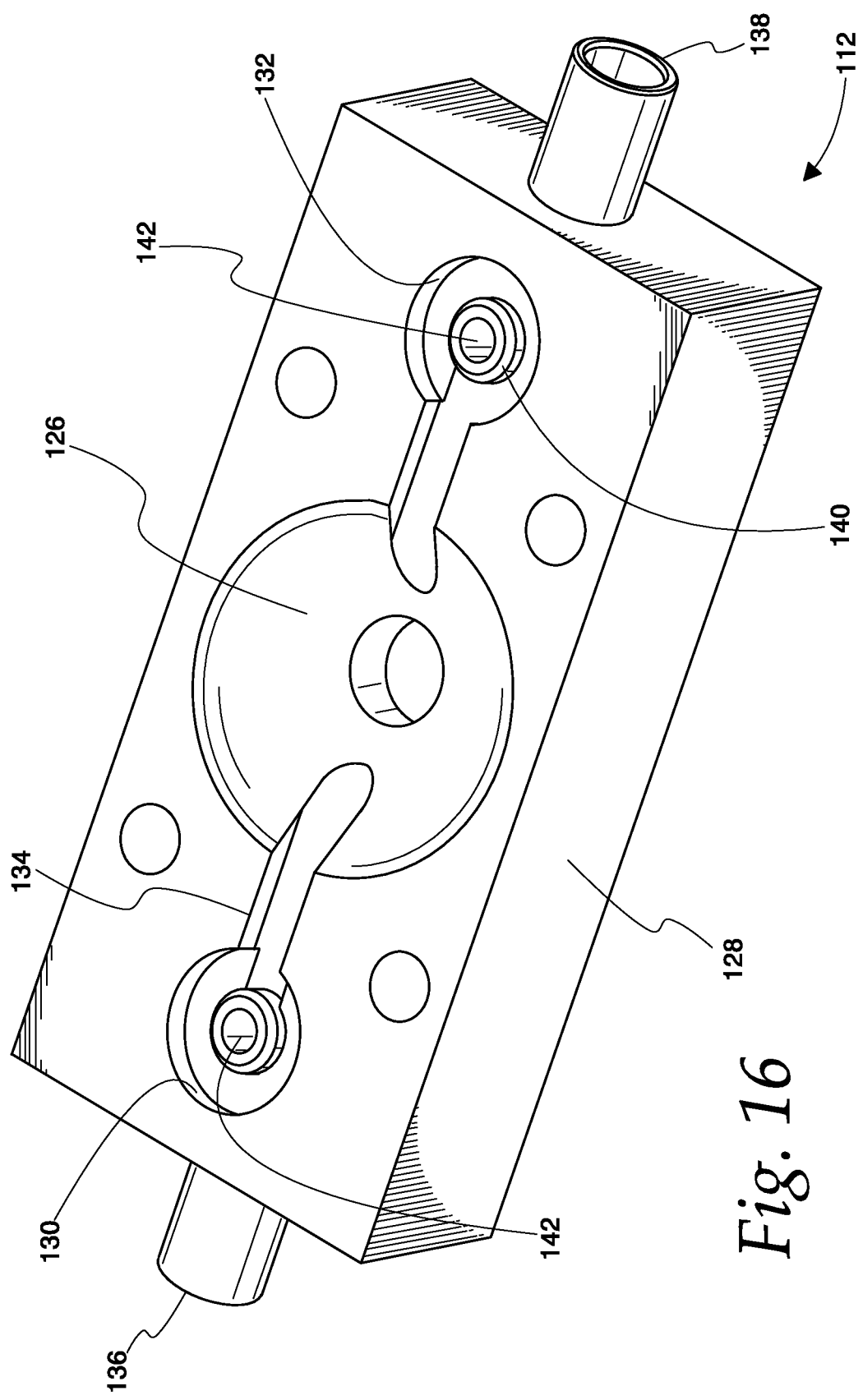
FIG. 16 is a bottom perspective view of the pump station of FIG. 14, with a flexible diaphragm thereof omitted for illustrative purposes.
Figure 17:
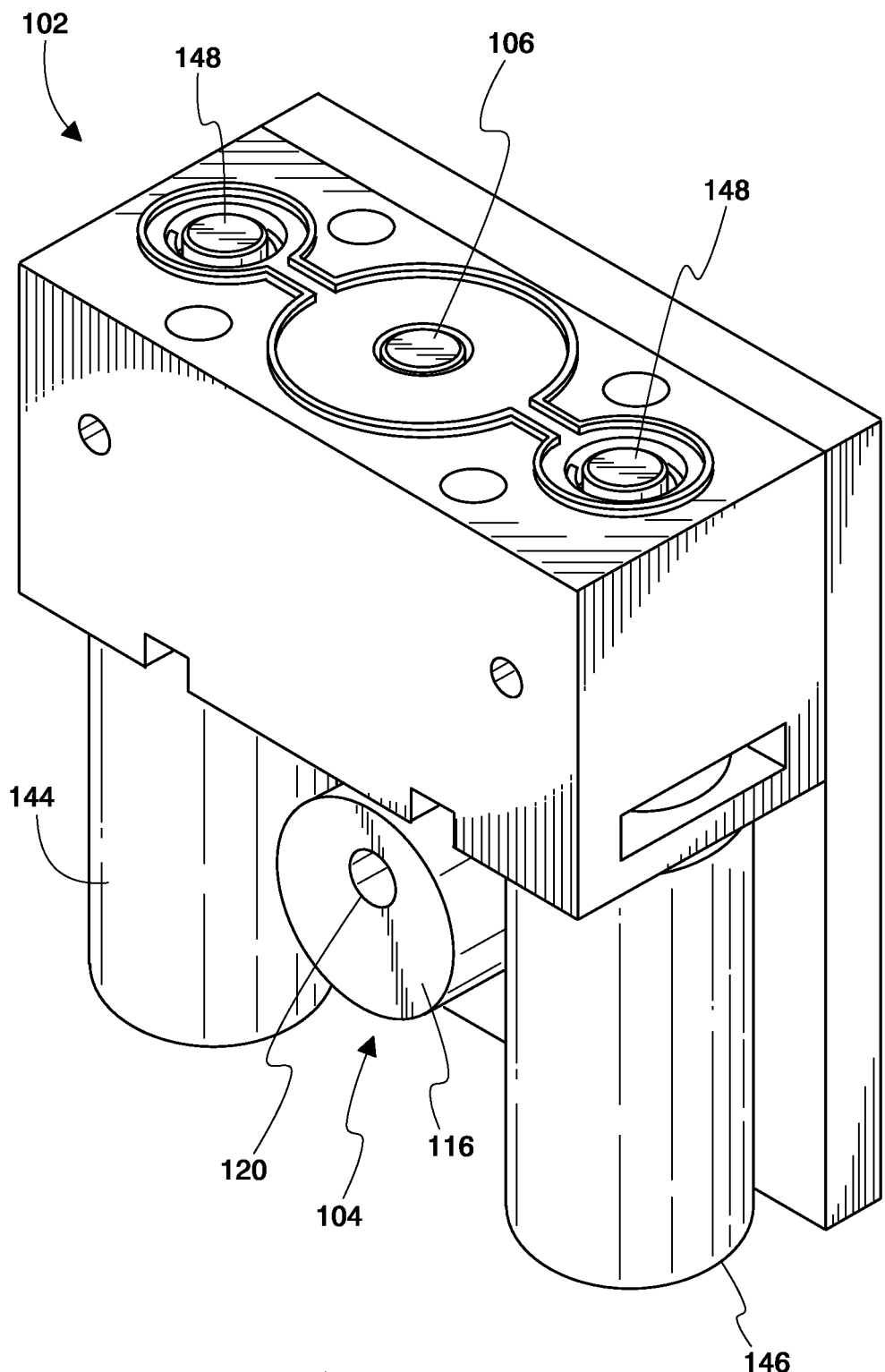
FIG. 17 is a perspective view of the fluid pump of FIG. 14, with the pump station of the fluid processing cassette omitted.
Figure 18:
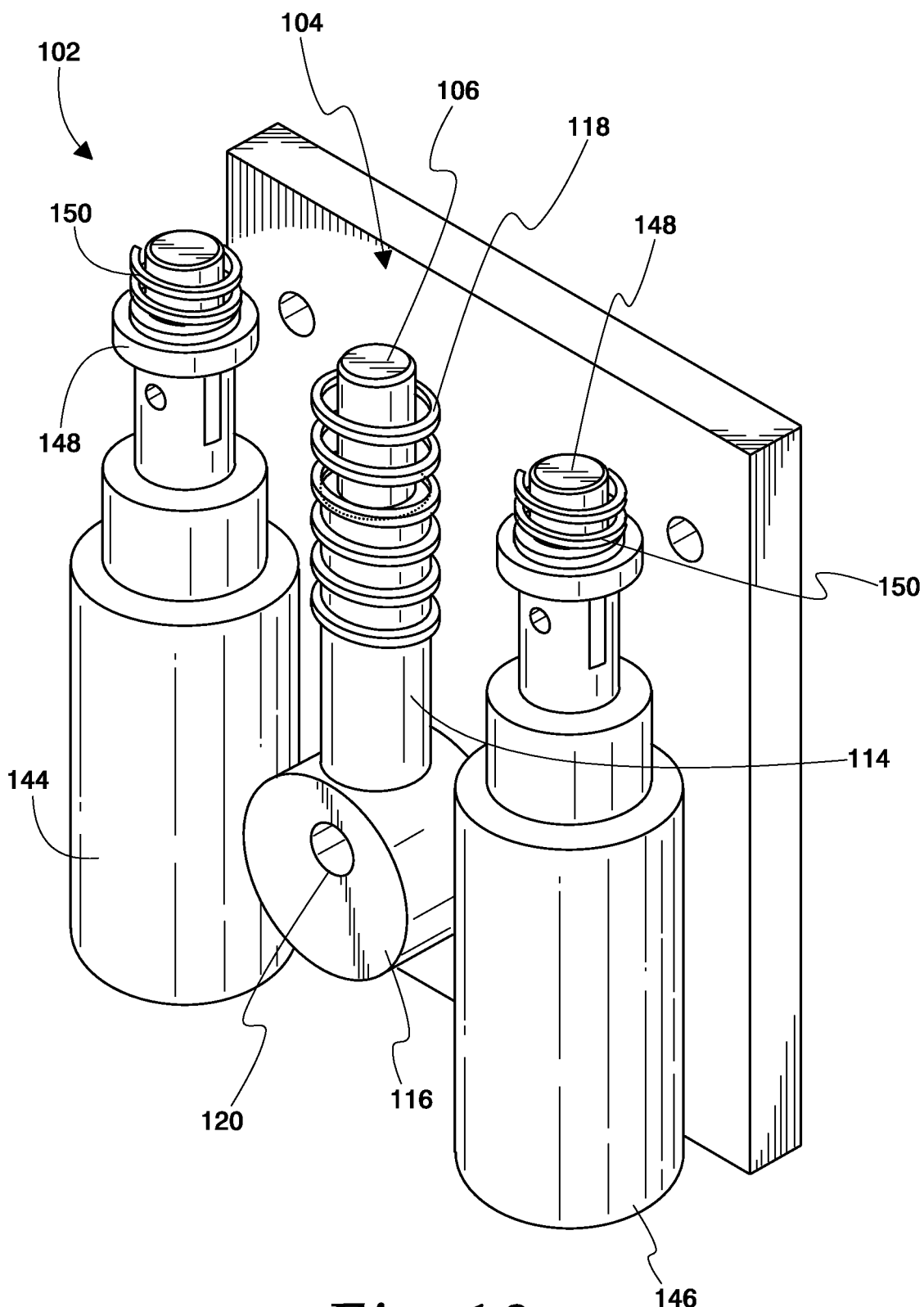
FIG. 18 is a perspective view of the fluid pump of FIG. 17, with a portion omitted for illustrative purposes.

The cassette 112 of FIGS. 14-16 differs from the cassette 18 of FIGS. 1-13, in that the body 128 of the cassette 112 may define one or more pump cavities 126 with additional valve cavities 130 and 132 in fluid communication with a pump cavity 126, as best shown in FIGS. 15 and 16. In the illustrated embodiment, the pump cavity 126 is associated with each valve cavity 130, 132 by a flow channel 134 defined by the body 128 of the cassette 112. Each valve cavity 130, 132, in turn, is provided in fluid communication with one of the ports 136, 138 (particularly, with valve cavity 130 being in fluid communication with port 136 and valve cavity 132 being in fluid communication with port 138). Each valve cavity 130, 132 is covered by the flexible diaphragm 110 and may include a raised valve seat 140 that may project or extend into the valve cavity 130, 132 toward the flexible diaphragm 110. In one embodiment, the valve seats 140 are generally annular, surrounding the entrance to a flow channel 142 connecting the valve cavity 130, 132 to the associated port 136, 138, but it is also within the scope of the present disclosure for the valve seats 140 to be differently configured.

The fluid transfer assembly 102 includes a valve actuator 144, 146 for each of the valve cavities 130, 132. Each valve actuator 144, 146 includes an actuator head 148 aligned with the valve seat 140 of the associated valve cavity 130, 132. The valve actuators 144 and 146 are movable (under the direction of a system controller) to move toward and away from the associated valve cavity 130, 132. When the port 136, 138 associated with the valve cavity 130, 132 is to be closed to prevent fluid flow into or out of the pump cavity 126 via the port 136, 138, the valve actuator 144, 146 associated with the valve cavity 130, 132 is moved to an extended or at least partially extended position in which the actuator head 148 presses the flexible diaphragm 110 covering the valve cavity 130, 132 into engagement with the valve seat 140. The outer surface of the actuator head 148 (i.e., the portion configured to contact the flexible diaphragm 110) is preferably larger than the opening of the flow channel 142, such that the flexible diaphragm 110 is pressed into engagement with the valve seat 140 by the actuator head 148 and completely covers the flow channel 142, thereby preventing fluid flow between the valve cavity 130, 132 and the associated port 136, 138.

When fluid flow into or out of the pump cavity 126 via a port 136, 138 is to be allowed, the valve actuator 144, 146 may be moved away from the flexible diaphragm 110 to a retracted or at least partially retracted position (as shown in FIG. 15). In the retracted or at least partially retracted position, the flexible diaphragm 110 is spaced away from the valve seat 140, thereby uncovering the flow channel 142 and allowing fluid flow between the port 136, 138 and the pump cavity 126. Similar to the fluid pump 104, each valve actuator 144, 146 may include a spring 150 or similar resilient element that biases the valve actuator 144, 146 into the retracted position of FIG. 15 (which may be advantageous if gravity tends to urge the actuator head 148 into contact with the diaphragm 110, such as if the valve actuators 144 and 146 are positioned above the cassette 112).

Preferably, the operation of the valve actuators 144 and 146 is synchronized with the movement of the motor by the system controller, such that one of the valve actuators 144, 146 is automatically operated to retract and allow fluid flow through the associated port 136, 138 at a particular motor state (which may correspond to the deployed position of the piston 106, for example), with the other valve actuator 144, 146 being automatically operated to retract and allow fluid flow through the associated port 136, 138 at a different motor state (which may correspond to the retracted position of the piston 106, for example). The operation of the valve actuators 144 and 146 with respect to the operation of the motor may be variously synchronized or associated without departing from the scope of the present disclosure.

In the illustrated embodiment, the flexible diaphragm 110 includes additional locations of magnetized or ferromagnetic material 152 (FIG. 15) where the diaphragm 110 overlays the valve cavities 130, 132. All or a portion of the actuator heads 148 may be magnetized or formed of a ferromagnetic material to interact with the magnetized or ferromagnetic material 152 overlaying the associated valve cavity 130, 132 in the same way that the magnetized or ferromagnetic piston 106 interacts with the corresponding magnetized or ferromagnetic material 108 of the diaphragm 110. By providing a magnetic relationship between the diaphragm 110 and the valve actuators 144 and 146, the valve actuators 144 and 146 actively pull the diaphragm 110 away from the valve seat 140 when moving away from the cassette 112 to allow fluid flow through the associated port 136, 138, rather than depending upon the resiliency of the flexible diaphragm 110 to unseat the diaphragm 110 from the valve seat 140 when the associated actuator head 148 is retracted.

It should be understood that the valving system of the embodiment of FIGS. 14-18 may be used in combination with any of the fluid pumps described herein or with any other fluid pump (including ones that do not involve a magnetic relationship between the fluid pump and the membrane of an associated fluid processing cassette). Additionally, it should be understood that, while the valve cavities 130 and 132 and the pump cavity 126 are shown as being covered by the same diaphragm 110, it is also within the scope of the present disclosure for different diaphragms to cover two or more of the various cavities of the cassette 112. Furthermore, while the magnetized or ferromagnetic materials 108 and 152 are illustrated as being embedded within the diaphragm 110, it is within the scope for them to be differently associated with the diaphragm 110 (including as illustrated in FIGS. 3 and 4) and for the different magnetized or ferromagnetic portions of the diaphragm 110 to be differently associated with the diaphragm 110.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing system, comprising:
a cassette including a body defining a rigid portion of a pump cavity in fluid communication with at least two ports, wherein a flexible diaphragm defines a flexible portion of the pump cavity; and
a fluid transfer assembly to which the cassette is configured to be temporarily secured, wherein the fluid processing system includes a fluid pump comprising
a motor,
a piston movable toward and away from the flexible diaphragm of the cassette, and
a linkage connecting the motor and the piston, wherein
the motor functions to move the piston toward and away from the flexible diaphragm,
at least a portion of the piston is magnetized and the flexible diaphragm comprises a ferromagnetic material positioned within the flexible diaphragm or said at least a portion of the piston is formed of said ferromagnetic material and the flexible diaphragm comprises a magnetized material positioned within the flexible diaphragm so as to magnetically couple the piston and the flexible diaphragm,
the rigid portion of the pump cavity includes a lower, substantially frusto-conical portion positioned adjacent to the flexible diaphragm and an upper, substantially cylindrical portion spaced from the flexible diaphragm by the lower, substantially frusto-conical portion, the upper, substantially cylindrical portion being aligned with the magnetized or ferromagnetic material positioned within the flexible diaphragm and with the piston when the cassette is secured to the fluid transfer assembly,
the cassette includes a valve cavity positioned between the pump cavity and one of said at least two ports, with a portion of the flexible diaphragm covering the valve cavity being magnetized or formed of said ferromagnetic material, and
the fluid transfer assembly further comprises a valve actuator aligned with the valve cavity and operable to move toward and away from the valve cavity to allow or prevent fluid flow through the valve cavity, with the valve actuator including an actuator head that is magnetized or formed of said ferromagnetic material so as to magnetically couple the actuator head and said portion of the flexible diaphragm.

2. A fluid processing cassette for use in combination with a fluid pump including a piston movable toward and away from the fluid processing cassette under operation of a motor, the fluid processing cassette comprising:
a body defining a rigid portion of a pump cavity;
a flexible diaphragm associated with and overlying the rigid portion of the pump cavity; and
a magnetized or ferromagnetic material positioned within the flexible diaphragm, wherein
the flexible diaphragm comprises first and second flexible sheets and the magnetized or ferromagnetic material comprises a magnetized or ferromagnetic member positioned between the first and second flexible sheets,
the first flexible sheet is entirely separated from the second flexible sheet, the magnetized or ferromagnetic member is secured to one or both of the first and second flexible sheets, and the first flexible sheet has a size and shape that are substantially the same as a size and shape of the second flexible sheet.

3. The fluid processing cassette of claim 2, wherein the magnetized or ferromagnetic material is primarily located at a central location of the diaphragm and in the middle of the pump cavity.

4. The fluid processing cassette of claim 2, wherein the rigid portion of the pump cavity is substantially frusto-conical.

5. A fluid processing system, comprising:
a cassette including a body defining a rigid portion of a pump cavity in fluid communication with at least two ports, wherein a flexible diaphragm defines a flexible portion of the pump cavity; and
a fluid transfer assembly to which the cassette is configured to be temporarily secured, wherein the fluid processing system includes a fluid pump comprising
a motor,
a piston movable toward and away from the flexible diaphragm of the cassette; and
a linkage connecting the motor and the piston, wherein the motor functions to move the piston toward and away from the flexible diaphragm,
at least a portion of the piston is magnetized and the flexible diaphragm comprises a ferromagnetic material positioned within the flexible diaphragm or said at least a portion of the piston is formed of said ferromagnetic material and the flexible diaphragm comprises a magnetized material positioned within the flexible diaphragm so as to magnetically couple the piston and the flexible diaphragm,
the rigid portion of the pump cavity includes a lower, substantially frusto-conical portion positioned adjacent to the flexible diaphragm and an upper, substantially cylindrical portion spaced from the flexible diaphragm by the lower, substantially frusto-conical portion, the upper, substantially cylindrical portion being aligned with the magnetized or ferromagnetic material positioned within the flexible diaphragm and with the piston when the cassette is secured to the fluid transfer assembly and configured to receive at least a portion of the magnetized or ferromagnetic material positioned within the flexible diaphragm when the piston is moved toward the flexible diaphragm,
a diameter of the upper, substantially cylindrical portion is substantially equal to a minimum diameter of the lower, substantially frusto-conical portion and approximately equal to a diameter of the magnetized or ferromagnetic material positioned within the flexible diaphragm,
the upper, substantially cylindrical portion includes a closed upper end, and
the body of the cassette defines at least two flow channels, with each flow channel extending between a different one of said at least two ports and the lower, substantially frusto-conical portion.

6. The fluid processing system of claim 5, wherein a height of the upper, substantially cylindrical portion is greater than a height of the magnetized or ferromagnetic material positioned within the flexible diaphragm.

7. The fluid processing system of claim 5, wherein
the piston is configured to pull the flexible diaphragm away from the rigid portion of the pump cavity upon sufficient movement of the piston away from the flexible diaphragm to decrease the pressure within the pump cavity to a vacuum condition,
one of the at least two ports includes a valve configured to open when the pressure within the pump cavity decreases to the vacuum condition, and
another one of the at least two ports includes a valve configured to close when the pressure within the pump cavity decreases to the vacuum condition.

8. The fluid processing system of claim 5, wherein
the piston is configured to press the flexible diaphragm toward the rigid portion of the pump cavity upon sufficient movement of the piston toward the flexible diaphragm to increase a pressure within the pump cavity,
one of the at least two ports includes a valve configured to open when the pressure within the pump cavity increases, and
another one of the at least two ports includes a valve configured to close when the pressure within the pump cavity increases.

9. The fluid processing system of claim 5, wherein said ferromagnetic or magnetized material positioned within the flexible diaphragm is embedded within the flexible diaphragm.

10. The fluid processing system of claim 5, wherein the flexible diaphragm comprises first and second flexible sheets and said ferromagnetic or magnetized material positioned within the flexible diaphragm comprises a magnetized or ferromagnetic member positioned between the first and second flexible sheets.

11. The fluid processing system of claim 5, wherein the piston is configured to become magnetically coupled to the flexible diaphragm upon contact between the piston and the flexible diaphragm.

12. The fluid processing system of claim 5, wherein the piston is configured to become magnetically coupled to the flexible diaphragm without contact between the piston and the flexible diaphragm.

13. The fluid processing system of claim 5, wherein said linkage comprises
a follower connected to the piston, and
a cam connected to a driveshaft of the motor, with the follower positioned in contact with the cam.

14. The fluid processing system of claim 13, further comprising a spring biasing the follower into contact with the cam.

15. The fluid processing system of claim 5, wherein said linkage comprises a connecting rod connected to the piston and a crankshaft connected to the connecting rod and to a driveshaft of the motor.

16. The fluid processing system of claim 15, wherein the motor is configured to rotate the driveshaft and the crankshaft in only a counterclockwise direction or only a clockwise direction.

17. The fluid processing system of claim 15, wherein the motor is configured to rotate the driveshaft and the crankshaft in two alternating directions.

* * * * *